United States Patent
Sato et al.

(10) Patent No.: US 11,172,901 B2
(45) Date of Patent: *Nov. 16, 2021

(54) TOMOSYNTHESIS IMAGING APPARATUS AND METHOD FOR OPERATING THE SAME

(71) Applicant: FUJIFILM Corporation, Tokyo (JP)

(72) Inventors: Masaru Sato, Kanagawa (JP); Masayoshi Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/565,496

(22) Filed: Sep. 10, 2019

(65) Prior Publication Data
US 2020/0100745 A1  Apr. 2, 2020

(30) Foreign Application Priority Data

Sep. 27, 2018  (JP) .............................. JP2018-182572

(51) Int. Cl.
  *A61B 6/04*  (2006.01)
  *A61B 6/00*  (2006.01)
  (Continued)

(52) U.S. Cl.
  CPC .............. *A61B 6/502* (2013.01); *A61B 6/025* (2013.01); *A61B 6/0414* (2013.01); *A61B 6/0435* (2013.01); *A61B 6/107* (2013.01)

(58) Field of Classification Search
  CPC ....... A61B 6/025; A61B 6/027; A61B 6/0414; A61B 6/0435; A61B 6/107; A61B 6/4007;
  (Continued)

(56) References Cited

U.S. PATENT DOCUMENTS 7,844,032 B2 * 11/2010 Vermilyea ............... H01J 35/16
                                                        378/149
9,649,074 B2    5/2017 Simon et al.
(Continued)

FOREIGN PATENT DOCUMENTS

JP    2011036399    2/2011
JP    2013230404    11/2013
(Continued)

OTHER PUBLICATIONS

Office Action of Japan Counterpart Application, with English translation thereof, dated May 11, 2021, pp. 1-6.

*Primary Examiner* — Irakli Kiknadze
(74) *Attorney, Agent, or Firm* — JCIPRNET

(57) ABSTRACT

A pre-imaging control unit of a mammography apparatus selects one pre-imaging focus from plural focuses of a radiation source according to selection conditions which are preset in order to prevent the concentration of load on one of the focuses. Pre-imaging for setting the irradiation conditions of radiation in tomosynthesis imaging is performed using the selected pre-imaging focus. For example, the selection conditions indicate that the pre-imaging focus is changed in each pre-imaging operation and the focus of a radiation tube adjacent to the radiation tube whose focus has been used in the previous pre-imaging is selected as the pre-imaging focus.

22 Claims, 25 Drawing Sheets

(51) Int. Cl.
*A61B 6/02* (2006.01)
*A61B 6/10* (2006.01)

(58) Field of Classification Search
CPC ....... A61B 6/4441; A61B 6/448; A61B 6/502; A61B 6/5205; A61B 17/8071; A61B 2017/00004; A61B 2034/104; A61B 2034/105; A61B 2034/108; A61B 34/10; A61B 6/4417; A61B 6/544; A61B 6/488; A61B 6/5217; A61B 6/542; A61B 6/545; A61B 6/583; A61B 6/461; A61B 6/467; A61B 6/5235; A61B 6/54; A61B 8/0825; A61B 34/30; A61B 5/055; A61B 6/037; A61B 6/4429; A61B 6/5211; A61B 6/405; A61B 6/508; A61B 6/4452; A61B 6/5427; A61B 6/4035; A61B 6/032; A61B 6/4405; A61B 6/4411; A61B 6/482; A61B 10/04; A61B 6/12; A61B 6/42; A61B 6/4208; A61B 6/4258; A61B 6/5247; A61B 6/06; A61B 6/08; A61B 6/4233; A61B 6/4283; A61B 6/481; A61B 6/505; A61B 6/5241; A61B 6/547; A61B 6/548; A61B 23/046; A61B 6/102; A61B 6/4028; A61B 6/4085; A61B 6/4014; A61B 6/4071; A61B 6/4458; A61B 6/5264; A61B 6/04; A61B 6/145; A61B 6/463; A61B 6/466; A61B 6/469; A61B 6/40; A61B 6/46; A61B 6/465; A61B 6/4266; A61B 6/44; A61B 6/022; A61B 6/0492; A61B 6/105; A61B 6/4291; A61B 6/58; H01J 35/08; H01J 2235/068; H01J 2235/086; H01J 2235/1204; H01J 2235/1262; H01J 35/16; H01J 2235/163; H01J 2235/166; H01J 35/04; H01J 35/06; H01J 2201/3165; H01J 2329/00; H01J 9/52; H01J 2235/083; H01J 35/108; H01J 2235/06; H01J 2237/121; H01J 2237/151; H01J 2237/153; H01J 2237/3175; H01J 37/12; H01J 37/3174; H01J 3/18; H01J 2201/30469; H01J 2235/062; G21K 1/025; A61C 13/0006; A61C 7/14; A61C 8/0012; A61C 8/0048; A61C 8/0096; G01N 23/046; G01N 23/044; G01N 2223/309; G01N 23/04; G01N 2223/401; G01N 2223/612; G01N 2223/6123; G01N 2223/6126; G01N 2223/03; G01N 2223/206; G01N 2223/3302; G01N 2223/405; G01N 2223/408; G01N 2223/419; G01N 2223/601; G01N 23/083; G01N 23/20075; G01N 2223/50; G01N 21/359; G01N 21/6456; G01N 2223/301; A61M 5/007; G01T 23/046; G01T 1/2018; G01T 2207/10116; G01T 2207/20224; G01T 2207/30101; G01T 5/50; H04N 5/32; H04N 21/41422; H04N 21/6131; H04N 21/6437; H04N 21/8456; A61N 5/1049; A61N 2005/1061; A61N 5/1067; A61N 5/1083; A61N 2005/1051; A61N 2005/1059; A61N 5/1065; A61N 5/1068; H05G 1/70; G06T 11/006; G06T 11/003; G06T 2207/10112; G06T 2207/30004; G06T 2207/30068; G06T 2211/436; G06T 11/005; G16H 50/50
USPC ............ 378/37, 62, 112, 123, 124, 136–138
See application file for complete search history.

(56) References Cited

U.S. PATENT DOCUMENTS

| | | | |
|---|---|---|---|
| 10,660,580 B2 | 5/2020 | Heath et al. | |
| 2007/0036265 A1* | 2/2007 | Jing | A61B 6/4028 378/37 |
| 2009/0022264 A1* | 1/2009 | Zhou | A61B 6/025 378/5 |
| 2010/0091940 A1* | 4/2010 | Ludwig | A61B 6/502 378/22 |
| 2011/0069812 A1* | 3/2011 | Takahashi | A61B 6/4464 378/21 |
| 2013/0077749 A1* | 3/2013 | Akahori | A61B 6/527 378/62 |
| 2013/0208852 A1* | 8/2013 | Koishi | A61B 6/548 378/19 |
| 2015/0004312 A1 | 1/2015 | Scheer et al. | |
| 2016/0007943 A1* | 1/2016 | Hoernig | A61B 6/482 378/37 |
| 2016/0181053 A1 | 6/2016 | Wang et al. | |
| 2016/0256128 A1* | 9/2016 | Wang | A61B 6/54 |
| 2020/0100746 A1* | 4/2020 | Sato | A61B 6/54 |

FOREIGN PATENT DOCUMENTS

| | | |
|---|---|---|
| JP | 2016501080 | 1/2016 |
| JP | 2016503721 | 2/2016 |
| JP | 2016135319 | 7/2016 |
| WO | 2010028208 | 3/2010 |

* cited by examiner

FIG. 7

TOMOSYNTHESIS IMAGING APPARATUS AND METHOD FOR OPERATING THE SAME

CROSS-REFERENCE TO RELATED APPLICATION

This application claims priority from Japanese Patent Application No. 2018-182572, filed Sep. 27, 2018, the disclosure of which is incorporated herein by reference in its entirety.

BACKGROUND

Technical Field

The technology according to the present disclosure relates to a tomosynthesis imaging apparatus and a method for operating the same.

Related Art

A tomosynthesis imaging apparatus has been known which performs tomosynthesis imaging that moves a radiation source to a plurality of positions with respect to a radiation detector and emits radiation from the radiation source at each position (for example, see JP2016-135319A). The focuses of the radiation at the plurality of positions to which the radiation source is moved are set so as to be arranged, for example, in an arc shape at equal intervals. In the tomosynthesis imaging, the radiation is emitted to an imaging surface of the radiation detector at a plurality of irradiation angles and a plurality of projection images of an object irradiated with the radiation at different irradiation angles are captured. Then, tomographic images in any tomographic planes of the object are generated on the basis of the plurality of projection images.

The tomosynthesis imaging apparatus disclosed in JP2016-135319A is a mammography apparatus that uses the breast as the object. The radiation source includes one radiation tube having one focus and the radiation source including the one radiation tube is moved to each position. Paragraphs [0021] and [0022] disclose a configuration in which pre-imaging is performed with a lower dose and for a shorter irradiation time than tomosynthesis imaging before the tomosynthesis imaging and the irradiation conditions of radiation in the tomosynthesis imaging are set on the basis of an image obtained by the pre-imaging.

In the tomosynthesis imaging apparatus according to the related art, such as the tomosynthesis imaging apparatus disclosed in JP2016-135319A, the radiation source including one focus is moved to each position. Therefore, there is a problem that the imaging time is relatively long and a burden on the subject increases.

For this reason, the inventors have examined a tomosynthesis imaging apparatus comprising a radiation source having a plurality of focuses. However, in a case in which the radiation source includes a plurality of focuses, the following problems related to pre-imaging have been found. The problems have not occurred in the radiation source according to the related art which has one focus.

That is, in a case in which one of the plurality of focuses is used for both pre-imaging and tomosynthesis imaging, load is concentrated on the one focus used for both pre-imaging and tomosynthesis imaging and the deterioration of the performance of the one focus is faster than that of other focuses.

An object of the technology according to the present disclosure is to provide a tomosynthesis imaging apparatus that can prevent the concentration of load on one focus in a case in which a radiation source includes a plurality of focuses of radiation and pre-imaging for setting the irradiation conditions of radiation in tomosynthesis imaging is performed and a method for operating the tomosynthesis imaging apparatus.

SUMMARY

In order to achieve the object, a tomosynthesis imaging apparatus according to the present disclosure comprises: a radiation detector that detects radiation transmitted through an object and has an imaging surface capturing a projection image of the object; a radiation source having a plurality of focuses of the radiation disposed at a plurality of positions where the radiation is emitted to the imaging surface at different irradiation angles; and a control unit that controls an operation of the radiation detector and the radiation source, selects one pre-imaging focus from the plurality of focuses according to selection conditions which are preset in order to prevent a concentration of load on one of the focuses, performs pre-imaging for setting irradiation conditions of the radiation in tomosynthesis imaging, which captures a plurality of projection images of the object at different irradiation angles, using the selected pre-imaging focus before the tomosynthesis imaging, and performs the tomosynthesis imaging using the plurality of focuses.

Preferably, the focuses of the radiation at the plurality of positions are set so as to be arranged in a linear shape or an arc shape at equal intervals.

Preferably, the radiation source includes a plurality of radiation tubes and at least one of the plurality of radiation tubes has one focus. Alternatively, it is preferable that the radiation source includes a plurality of radiation tubes and at least one of the plurality of radiation tubes has a plurality of the focuses.

Preferably, the selection conditions include a first condition that defines a time when the pre-imaging focus is changed and a second condition that defines which of the plurality of focuses is selected as the pre-imaging focus.

Preferably, the first condition indicates that the pre-imaging focus is changed in each pre-imaging operation.

Preferably, the first condition indicates that the pre-imaging focus is changed in a case in which the pre-imaging is continuously performed a set number of times using the same pre-imaging focus.

Preferably, the first condition indicates that the pre-imaging focus is changed in a case in which an actual value of a cumulative dose of the radiation in the pre-imaging is greater than a set value after the pre-imaging focus is changed in previous pre-imaging.

Preferably, the second condition indicates that a focus which has not been used as the pre-imaging focus in the previous pre-imaging is selected as the pre-imaging focus in next pre-imaging.

Preferably, the radiation source includes a plurality of radiation tubes each of which has at least one focus, and the second condition indicates that a focus of a radiation tube adjacent to the radiation tube whose focus has been used as the pre-imaging focus in the previous pre-imaging is selected as the pre-imaging focus in the next pre-imaging.

Preferably, the radiation source includes a plurality of radiation tubes each of which has at least one focus, the tomosynthesis imaging apparatus further comprises an acquisition unit that acquires a temperature of each of the plurality of radiation tubes, and the second condition indicates that a focus of a radiation tube with a lowest temperature is selected as the pre-imaging focus in the next pre-imaging.

Preferably, the tomosynthesis imaging apparatus further comprises a derivation unit that derives a degree of deterioration of a performance of each of the plurality of focuses on the basis of a usage history of each of the plurality of focuses. Preferably, the second condition indicates that a focus with a smallest degree of deterioration is selected as the pre-imaging focus in the next pre-imaging.

Preferably, the tomosynthesis imaging apparatus is a mammography apparatus that uses a breast as the object.

Preferably, the first condition indicates that the pre-imaging focus is changed according to imaging methods including craniocaudal imaging which captures an image of the breast compressed in a vertical direction, right mediolateral oblique imaging which captures an image of a right breast compressed obliquely, and left mediolateral oblique imaging which captures an image of a left breast compressed obliquely, and the second condition indicates that a focus closest to a position of a center of a maximum scanning angle of the tomosynthesis imaging which is defined by positions at both ends among the plurality of positions is selected as the pre-imaging focus in the craniocaudal imaging, a focus which is disposed at a position close to a right axilla of the positions at both ends is selected as the pre-imaging focus in the right mediolateral oblique imaging, and a focus which is disposed at a position close to a left axilla of the positions at both ends is selected as the pre-imaging focus in the left mediolateral oblique imaging.

Preferably, the tomosynthesis imaging apparatus further comprises an irradiation field limiter which sets an irradiation field of the radiation, whose number is less than the number of the plurality of focuses, and whose position is capable of being moved. Preferably, before the next pre-imaging starts, the irradiation field limiter is moved to a position of the pre-imaging focus in the next pre-imaging to set the irradiation field.

Preferably, the tomosynthesis imaging apparatus further comprises irradiation field limiters that set an irradiation field of the radiation, are provided for each of the plurality of focuses, and are capable of being individually operated. Preferably, before the next pre-imaging starts, the irradiation field limiter corresponding to the pre-imaging focus in the next pre-imaging is operated to set the irradiation field.

Preferably, the radiation source includes a cathode that emits electrons and an anode with which the electrons collide and which emits the radiation. Preferably, the anode is a fixed anode. Preferably, the cathode is a field emission type including an electron emission source that emits an electron beam using a field emission phenomenon.

According to the present disclosure, there is provided a method for operating a tomosynthesis imaging apparatus comprising a radiation detector that detects radiation transmitted through an object and has an imaging surface capturing a projection image of the object and a radiation source having a plurality of focuses of the radiation disposed at a plurality of positions where the radiation is emitted to the imaging surface at different irradiation angles. The method comprises: a pre-imaging control step of selecting one pre-imaging focus from the plurality of focuses according to selection conditions which are preset in order to prevent a concentration of load on one of the focuses and performing pre-imaging for setting irradiation conditions of the radiation in tomosynthesis imaging, which captures a plurality of projection images of the object at different irradiation angles, using the selected pre-imaging focus before the tomosynthesis imaging; and a tomosynthesis imaging control step of performing the tomosynthesis imaging using the plurality of focuses.

According to the technology of the present disclosure, it is possible to provide a tomosynthesis imaging apparatus that can prevent the concentration of load on one focus in a case in which a radiation source has a plurality of focuses and pre-imaging for setting the irradiation conditions of radiation in tomosynthesis imaging is performed and a method for operating the tomosynthesis imaging apparatus.

BRIEF DESCRIPTION OF THE DRAWINGS

Exemplary embodiments according to the technique of the present disclosure will be described in detail based on the following figures, wherein:

FIG. 7 is a diagram illustrating an aspect of tomosynthesis imaging;

DETAILED DESCRIPTION

First Embodiment

Figure 1:
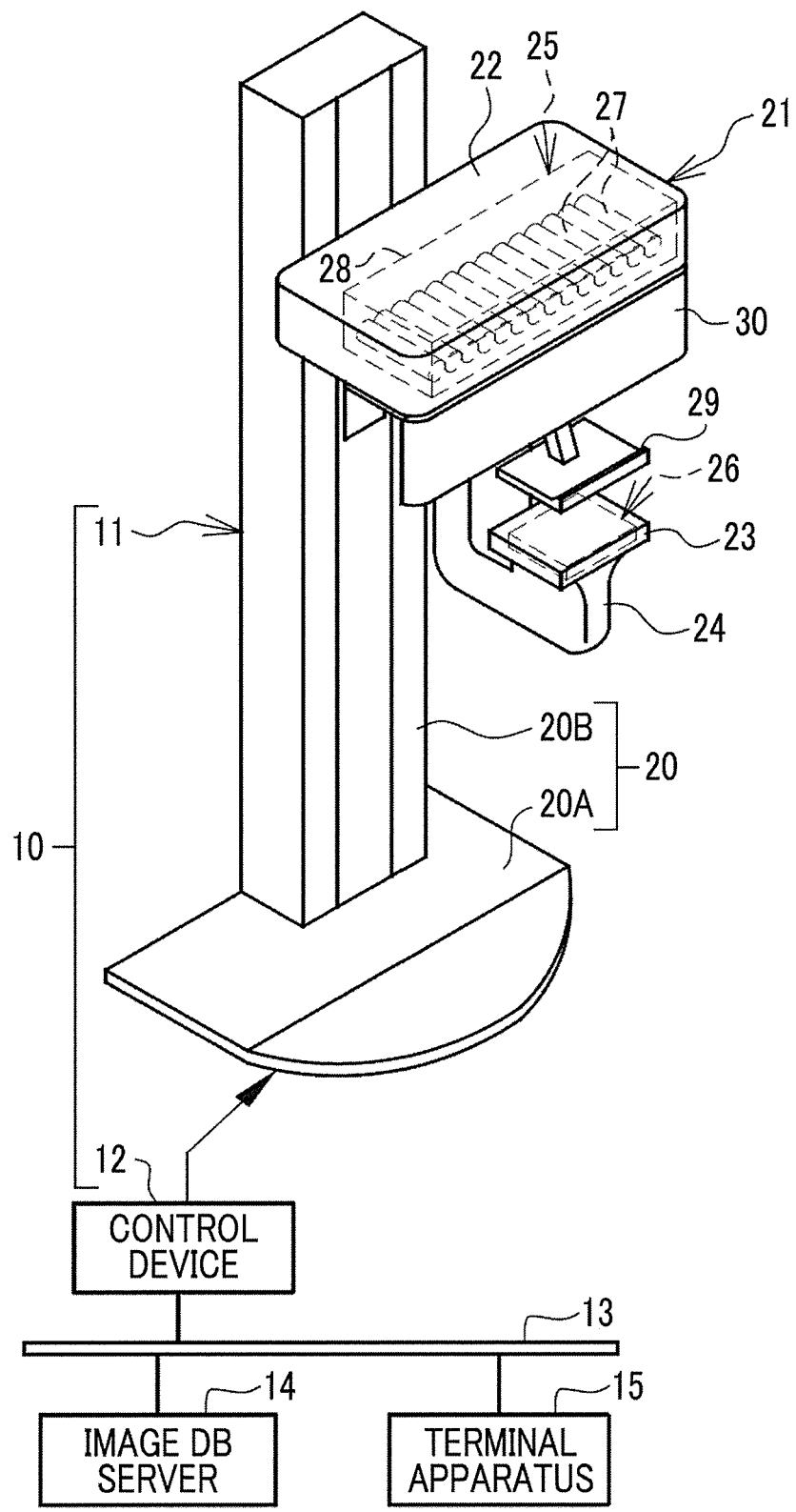
FIG. 1 is a diagram illustrating, for example, a mammography apparatus.
Figure 2:
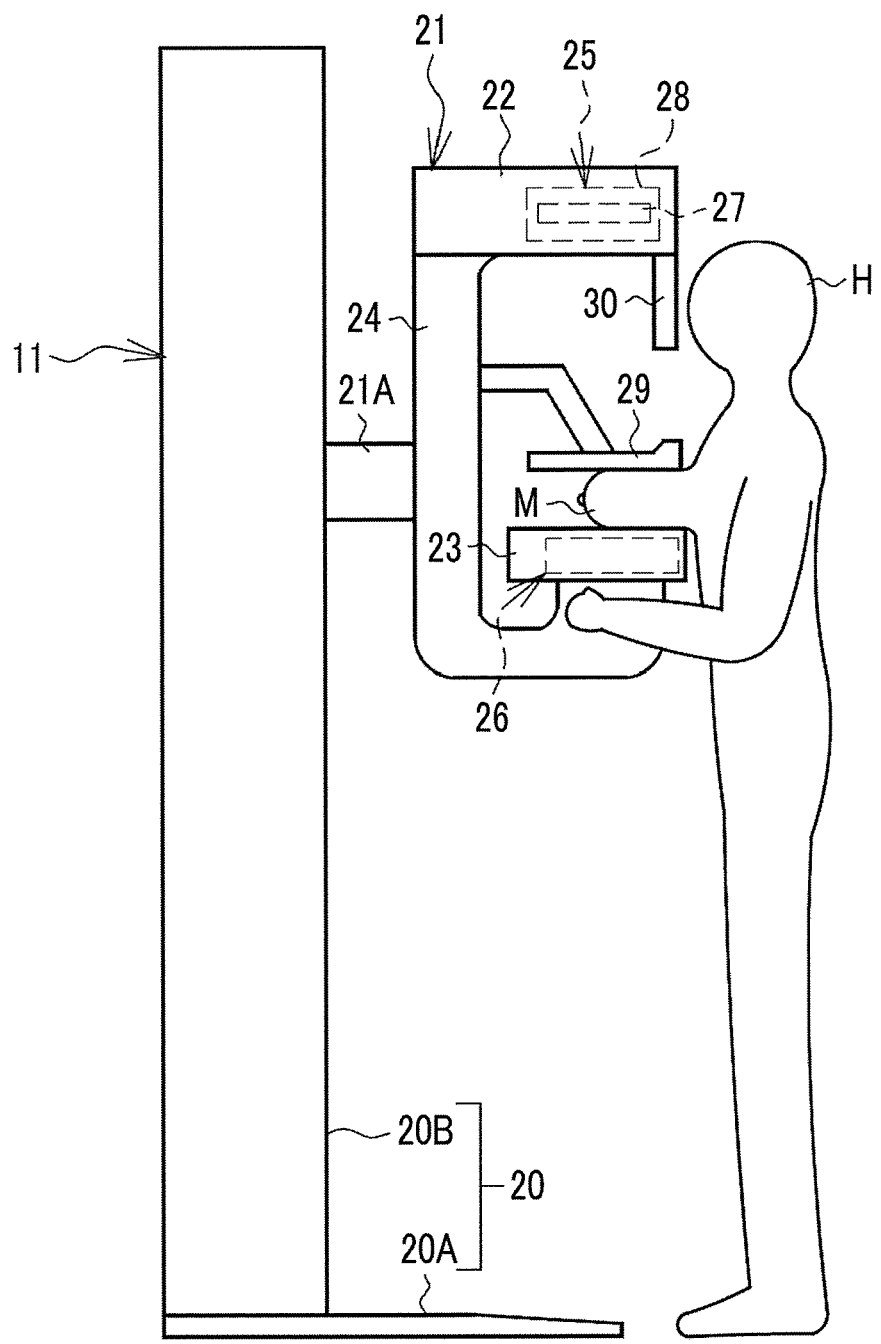
FIG. 2 is a diagram illustrating an apparatus main body of the mammography apparatus.

In FIGS. 1 and 2, a mammography apparatus 10 which is an example of a tomosynthesis imaging apparatus uses a breast M of a subject H as an object. The mammography apparatus 10 irradiates the breast M with radiation 37 (see, for example, FIG. 3), such as X-rays or γ-rays, to capture a radiographic image of the breast M.

The mammography apparatus 10 includes an apparatus main body 11 and a control device 12. The apparatus main body 11 is installed, for example, in a radiography room of a medical facility. The control device 12 is installed, for example, in a control room next to the radiography room. The control device 12 is connected to an image database (hereinafter, referred to as DB) server 14 through a network 13, such as a local area network (LAN), such that it can communicate with the image DB server. The image DB server 14 is, for example, a picture archiving and communication system (PACS) server, receives a radiographic image from the mammography apparatus 10, and accumulates and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes a plurality of radiation tubes 27, for example, 14 radiation tubes 27 and a housing 28 that accommodates the radiation tubes 27. The radiation tubes 27 are used for tomosynthesis imaging which captures a plurality of projection images of the breast M at different irradiation angles as radiographic images. One of the radiation tubes 27 is used for pre-imaging which is performed before the tomosynthesis imaging in order to set the irradiation conditions of the radiation 37 in the tomosynthesis imaging. The radiation detector 26 detects the radiation 37 transmitted through the breast M and outputs a radiographic image.

A compression plate 29 is attached between the radiation source accommodation portion 22 and the detector accommodation portion 23 in the main body portion 24. The compression plate 29 is made of a material that transmits the radiation 37. The compression plate 29 is provided so as to face the detector accommodation portion 23. The compression plate 29 can be moved in a direction toward the detector accommodation portion 23 and a direction away from the detector accommodation portion 23. The compression plate 29 is moved toward the detector accommodation portion 23 and compresses the breast M interposed between the detector accommodation portion 23 and the compression plate 29.

A face guard 30 is attached to a lower part of the front surface of the radiation source accommodation portion 22. The face guard 30 protects the face of the subject H from the radiation 37.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
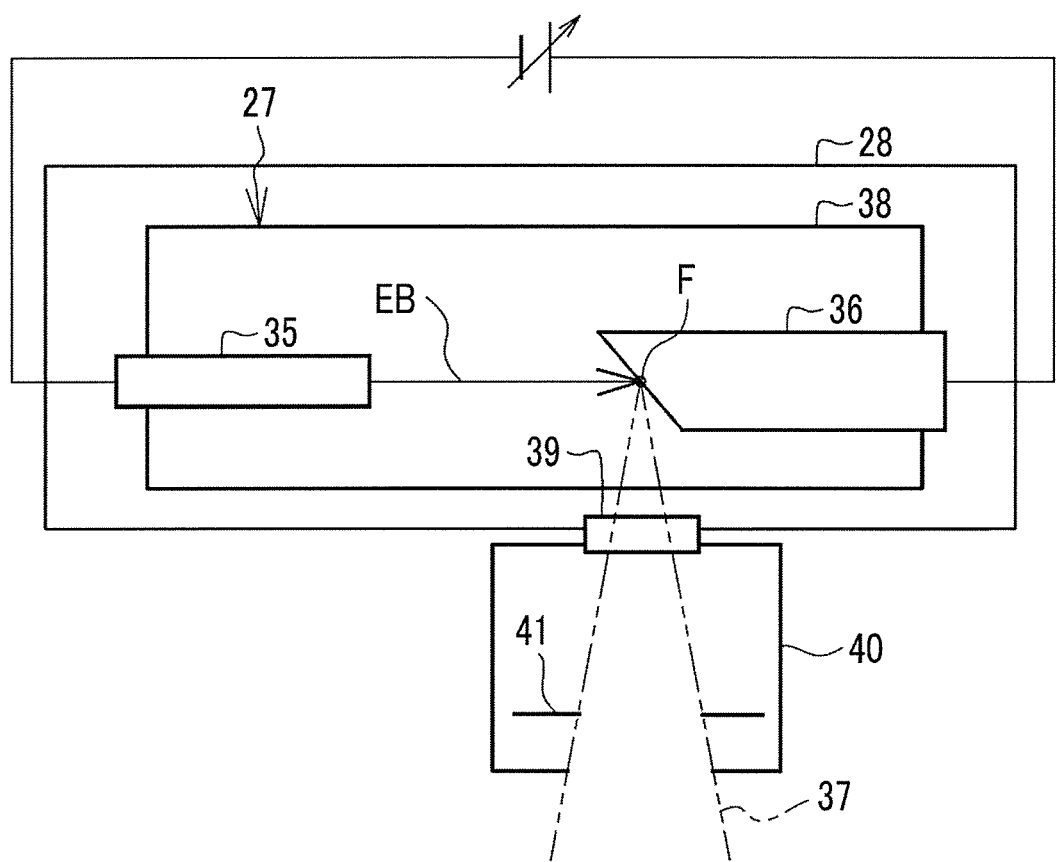
FIG. 3 is a diagram illustrating a radiation tube.

In FIG. 3, the radiation tube 27 includes a cathode 35 and an anode 36. The cathode 35 emits electrons. The electrons collide with the anode 36 and the anode 36 emits the radiation 37. The cathode 35 and the anode 36 are accommodated in a vacuum glass tube 38. The cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides. In this embodiment, each radiation tube 27 has one focus F.

The housing 28 is provided with a radiation transmission window 39 that transmits the radiation 37. The radiation 37 emitted from the anode 36 is emitted to the outside of the housing 28 through the radiation transmission window 39. In addition, the housing 28 is filled with insulating oil.

An irradiation field limiter 40 (not illustrated in FIGS. 1 and 2) is provided below the radiation transmission window 39 in the height direction. The irradiation field limiter 40 is also called a collimator and sets the irradiation field of the radiation 37 in an imaging surface 45 (see FIG. 4) of the radiation detector 26. Specifically, the irradiation field limiter 40 includes a plurality of shielding plates 41 which are made of, for example, lead and shield the radiation 37 transmitted through the radiation transmission window 39. The shielding plates 41 are moved to change the size of, for example, a rectangular irradiation opening defined by the shielding plates 41, thereby setting the irradiation field of the radiation 37.

Figure 7:
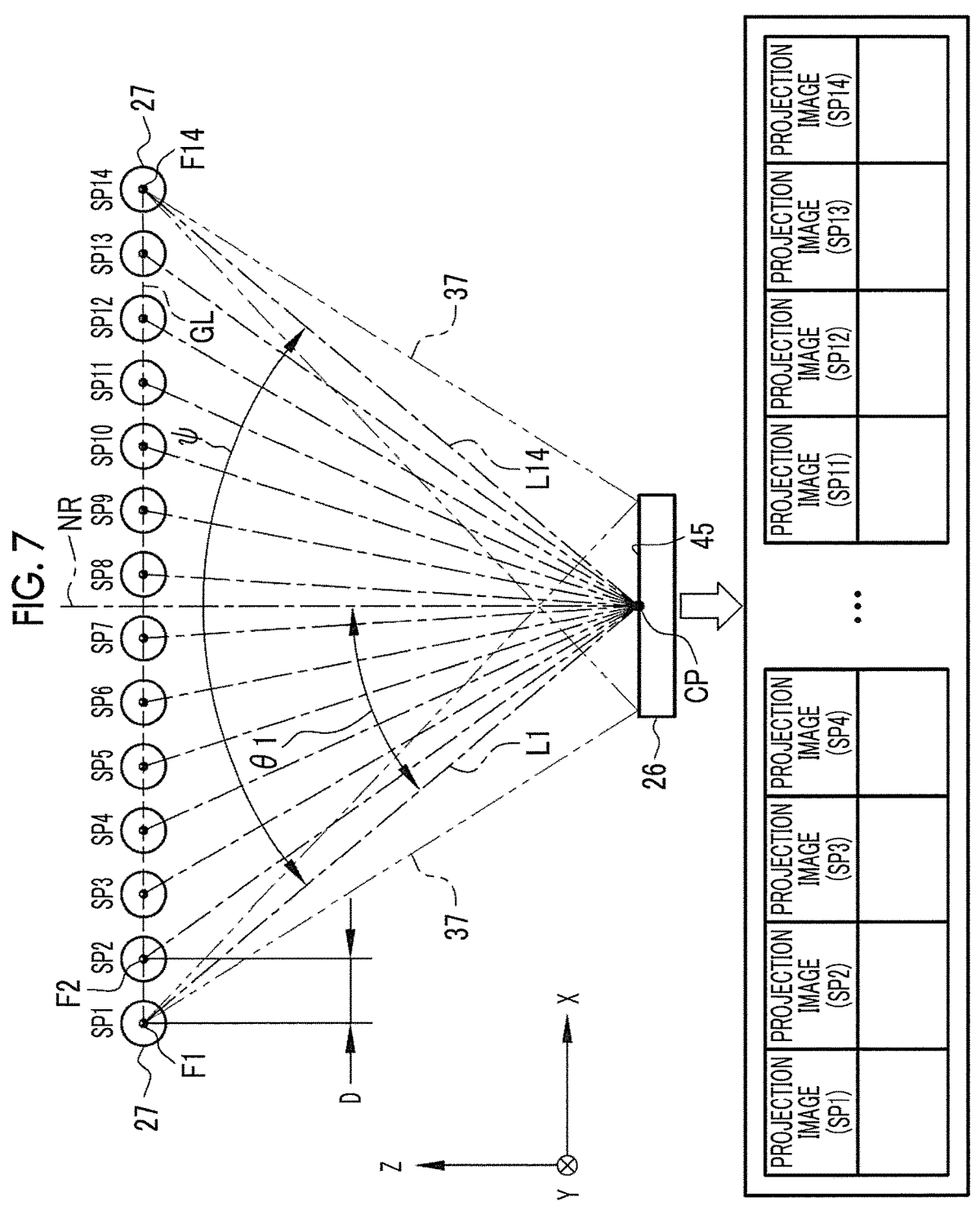

The number of irradiation field limiters 40 provided is less than the number of focuses F1 to F14 (see FIG. 7). For example, only one irradiation field limiter 40 is provided for a plurality of focuses F1 to F14. The irradiation field limiter 40 is moved immediately below each radiation tube 27 to individually set the irradiation field of the radiation 37 emitted from each of the focuses F1 to F14 of the radiation tubes 27.

Figure 4:
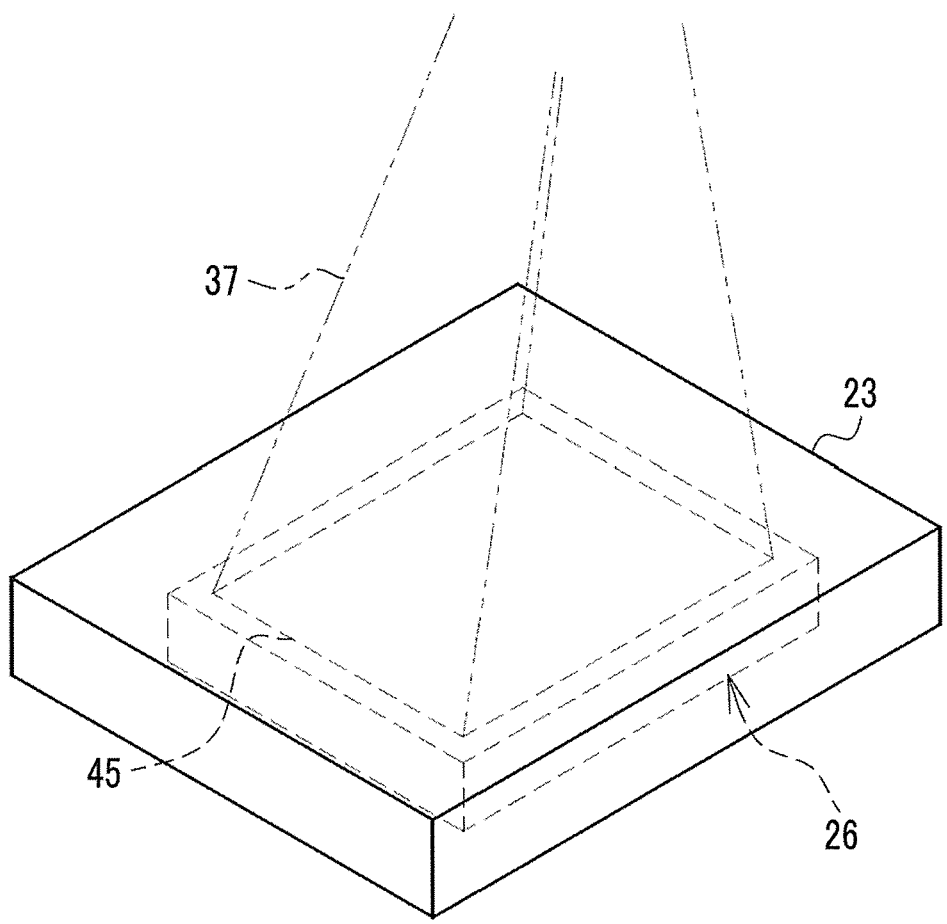
FIG. 4 is a diagram illustrating a detector accommodation portion.

In FIG. 4 illustrating the detector accommodation portion 23, the radiation detector 26 has the imaging surface 45. The imaging surface 45 detects the radiation 37 transmitted through the breast M and captures a projection image of the breast M. Specifically, the imaging surface 45 is a two-dimensional plane in which pixels converting the radiation 37 into an electric signal are two-dimensionally arranged. The radiation detector 26 is also referred to as a flat panel detector (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal.

Figure 5:
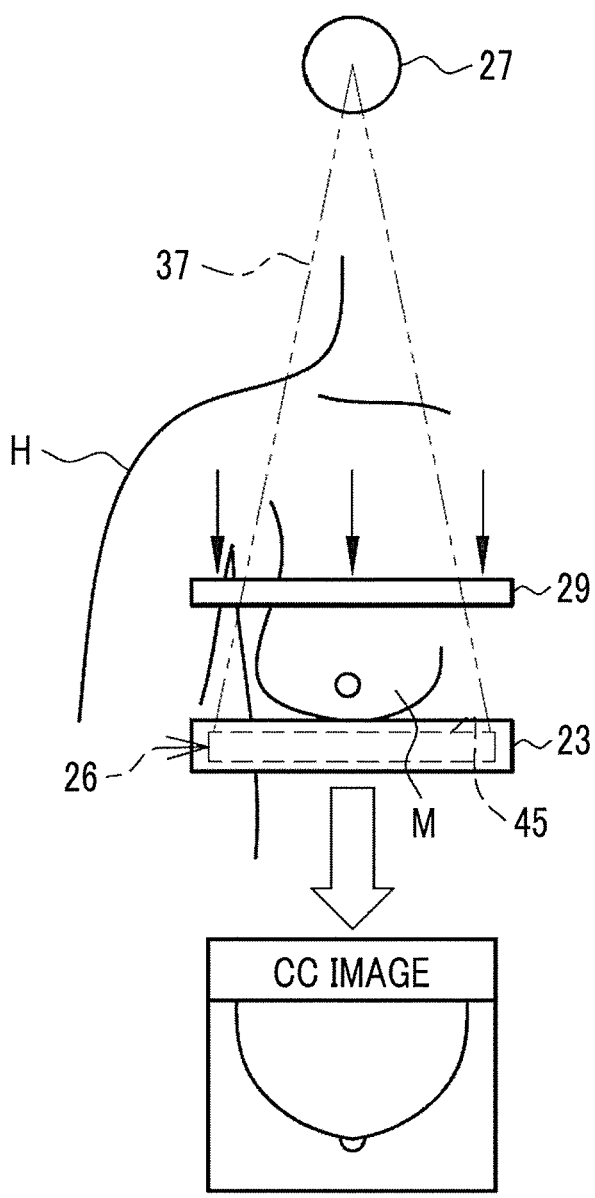
FIG. 5 is a diagram illustrating an aspect of CC imaging.
Figure 6:
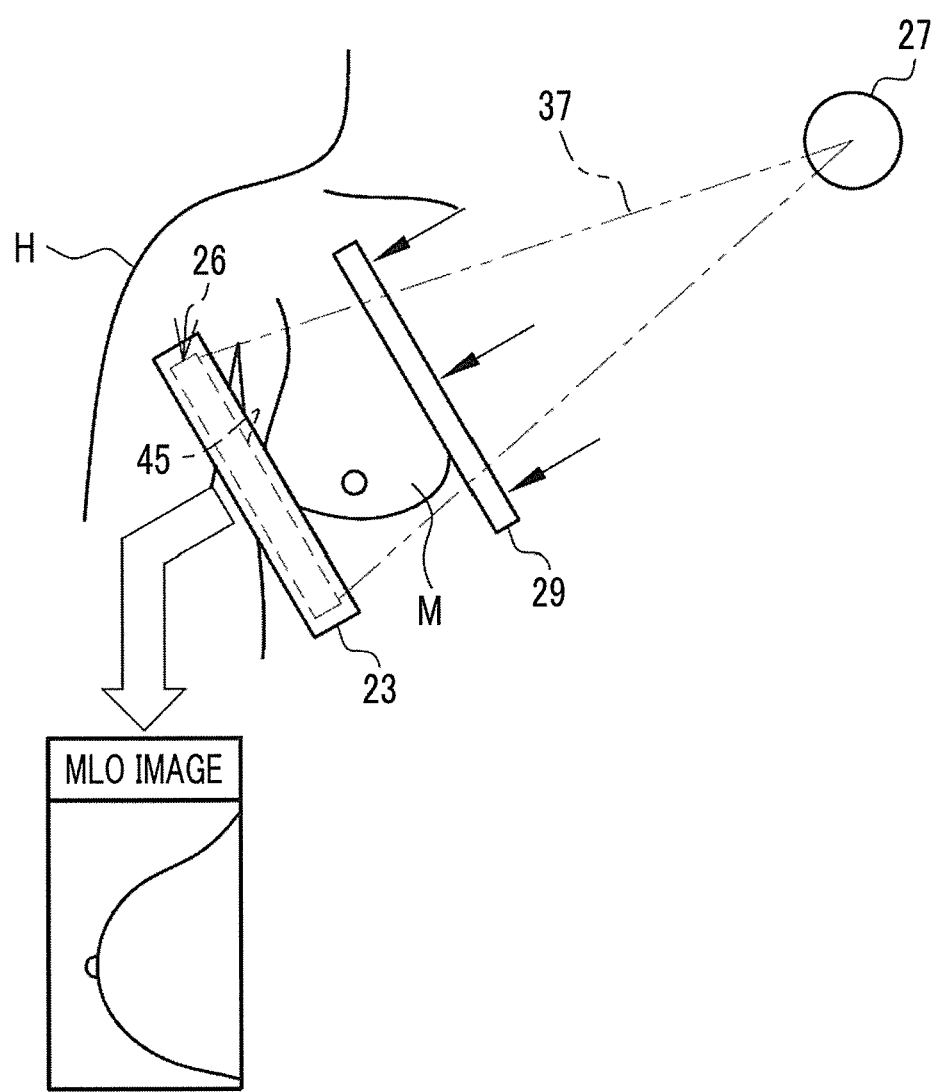
FIG. 6 is a diagram illustrating an aspect of MLO imaging.

FIGS. 5 and 6 illustrate a method for capturing an image of the breast M in the mammography apparatus 10. FIG. 5 illustrates craniocaudal view (CC) imaging and FIG. 6 illustrates mediolateral oblique view (MLO) imaging. The CC imaging is an imaging method which captures an image while compressing the breast M interposed between the detector accommodation portion 23 and the compression plate 29 in the vertical direction. In this case, the radiation detector 26 outputs a CC image as the projection image. In contrast, the MLO imaging is an imaging method which captures an image while compressing the breast M interposed between the detector accommodation portion 23 and the compression plate 29 at an inclination angle of about 60°. In this case, the radiation detector 26 outputs an MLO image as the projection image. In addition, FIGS. 5 and 6 illustrate only one radiation tube 27 for simplicity of illustration. Further, FIGS. 5 and 6 illustrate the right breast M. Of course, the image of the left breast M can be captured.

In FIG. 7 which is a plan view illustrating the radiation source 25 and the radiation detector 26 as viewed from the support 20B, it is assumed that the direction of a normal line to the imaging surface 45 is the Z direction, a direction along a side of the imaging surface 45 is the X direction, and a depth direction of the imaging surface 45 which is perpendicular to the Z direction and the X direction is the Y direction. The radiation tubes 27 are provided at a total of 14 positions SP1, SP2, ..., SP13, and SP14 where the radiation 37 is emitted to the imaging surface 45 at different irradiation angles. For the positions SP1 to SP14, the focuses F1 to F14 of the radiation 37 in the radiation tubes 27 at the positions SP1 to SP14 are set so as to be linearly arranged at equal intervals D. In addition, the positions SP1 to SP14 are bilaterally symmetric with respect to a normal line NR to the imaging surface 45 which extends from a center point CP of the side of the imaging surface 45 along the X direction such that the positions SP1 to SP7 are disposed on the left side of the normal line NR and the positions SP8 to SP14 are disposed on the right side of the normal line NR.

Here, a straight line GL on which the positions SP1 to SP14 are set is parallel to the side of the imaging surface 45 along the X direction in a plan view of the radiation source 25 and the radiation detector 26 from the Z direction. The straight line GL is offset to the front side (a side opposite to the support 20B) in the Y direction. The present disclosure is not limited to a case in which the intervals D between the focuses F1 to F14 are exactly equal to each other. For example, an error of ±5% is allowed.

The irradiation angle of the radiation 37 is an angle formed between the normal line NR and a line connecting the center point CP and each of the focuses F1 to F14 of the radiation 37 in the radiation tubes 27 at the positions SP1 to SP14. For example, FIG. 7 illustrates a line L1 connecting the focus F1 at the position SP1 and the center point CP and an irradiation angle θ1 formed between the normal line NR and the line L1.

An angle represented by a symbol ψ is the maximum scanning angle of tomosynthesis imaging. The maximum scanning angle ψ is defined by the positions SP1 and SP14 at both ends among the positions SP1 to SP14. Specifically, the maximum scanning angle ψ is an angle formed between the line L1 connecting the focus F1 at the position SP1 and the center point CP and a line L14 connecting the focus F14 at the position SP14 and the center point CP.

In one tomosynthesis imaging operation, the radiation tubes 27 are driven one by one in the order of the radiation tube 27 at the position SP1, the radiation tube 27 at the position SP2, ..., the radiation tube 27 at the position SP13, and the radiation tube 27 at the position SP14 to irradiate the breast M with the radiation 37. The radiation detector 26 detects the radiation 37 emitted at each of the positions SP1 to SP14 whenever the radiation 37 is emitted and outputs projection images at the positions SP1 to SP14. The tomosynthesis imaging can be performed by both the CC imaging method illustrated in FIG. 5 and the MLO imaging method illustrated in FIG. 6. In the case of simple imaging in which the CC imaging illustrated in FIG. 5 and the MLO imaging illustrated in FIG. 6 are independently performed, the radiation tube 27 at the position SP7 or the position SP8 where the irradiation angle θ is approximately 0° is used.

Figure 8:
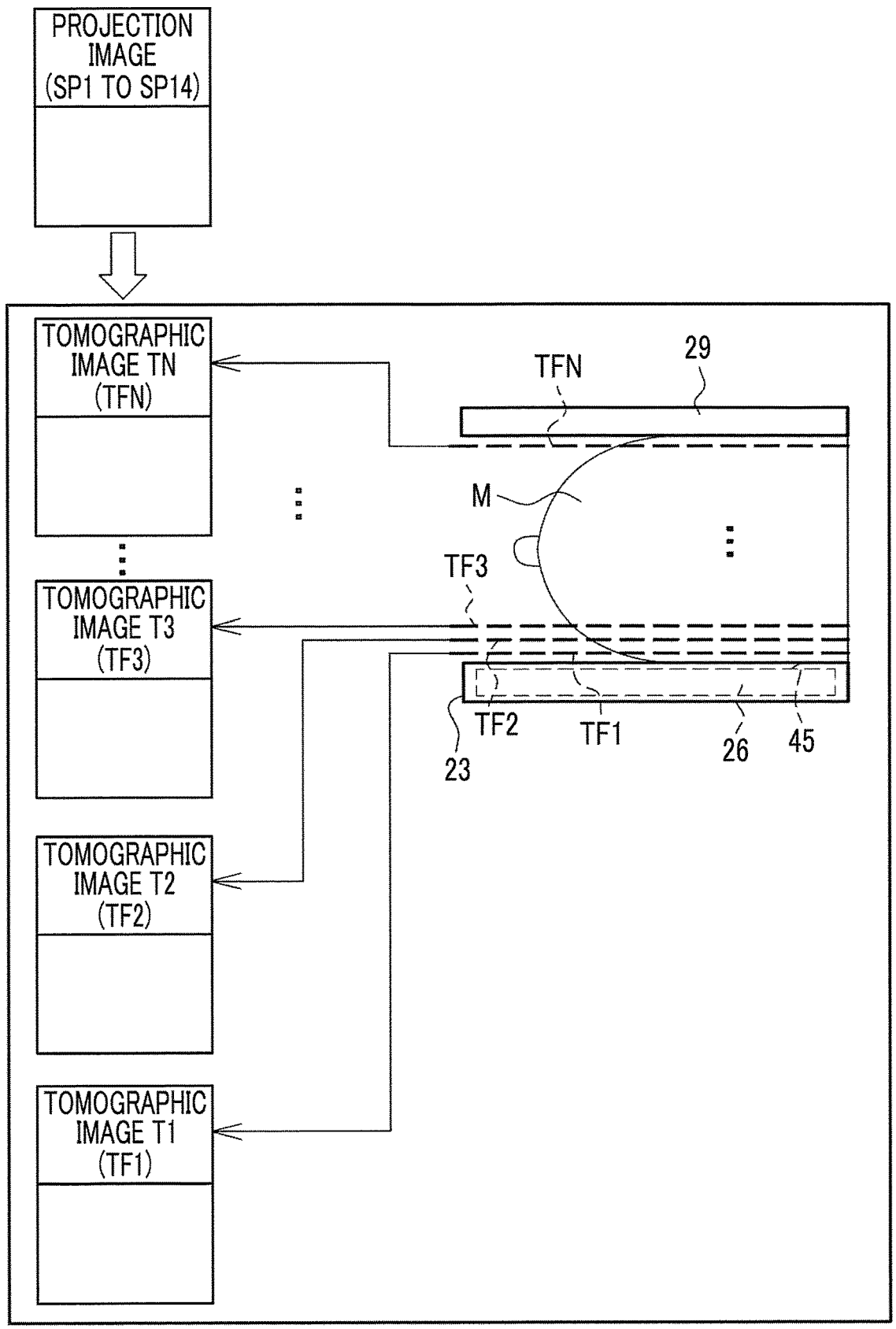
FIG. 8 is a diagram illustrating an aspect in which tomographic images are generated from a plurality of projection images obtained by the tomosynthesis imaging.

As illustrated in FIG. 8, the mammography apparatus 10 generates tomographic images T1 to TN corresponding to any tomographic planes TF1 to TFN of the breast M from the plurality of projection images at the plurality of positions SP1 to SP14 obtained by the tomosynthesis imaging illustrated in FIG. 7, using a known method such as a filtered back projection method. In the tomographic images T1 to TN, images in which structures in the tomographic planes TF1 to TFN have been highlighted are obtained.

Figure 9:
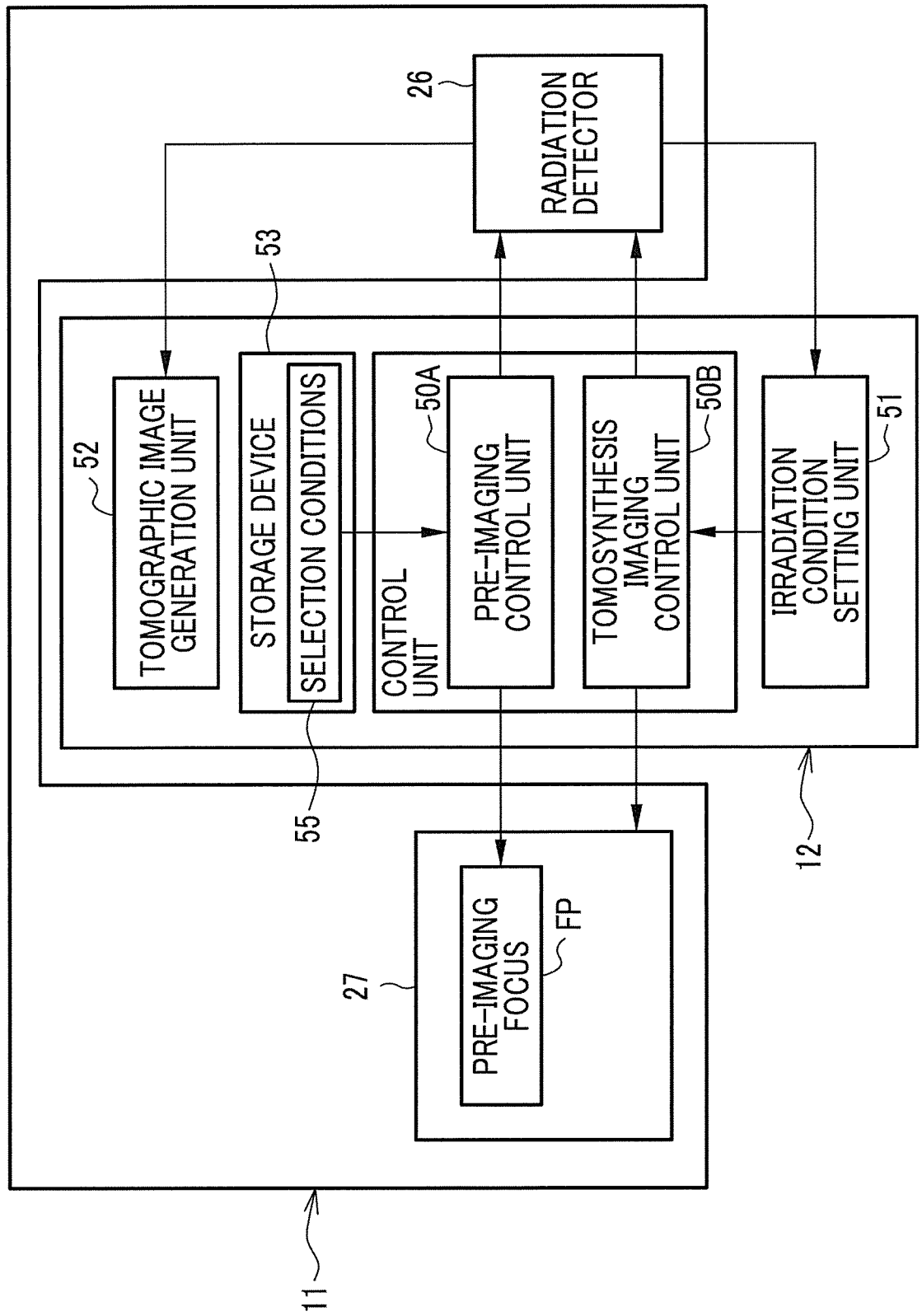
FIG. 9 is a block diagram illustrating a control device.

In FIG. 9, the control device 12 comprises a control unit 50, an irradiation condition setting unit 51, a tomographic image generation unit 52, and a storage device 53. The storage device 53 is, for example, a hard disk drive.

The control unit 50 controls the operation of the radiation source 25 and the radiation detector 26. The control unit 50 is provided with a pre-imaging control unit 50A and a tomosynthesis imaging control unit 50B. The pre-imaging control unit 50A performs pre-imaging using a pre-imaging focus FP. Specifically, the pre-imaging control unit 50A selects a pre-imaging focus FP used for pre-imaging from the plurality of focuses F1 to F14 according to selection conditions 55 stored in the storage device 53. Then, the pre-imaging control unit 50A drives the radiation tube 27 having the pre-imaging focus FP under the preset irradiation conditions for pre-imaging such that the radiation 37 is emitted from the pre-imaging focus FP of the radiation tube 27. Then, a projection image detected by the radiation detector 26 is output from the radiation detector 26 to the irradiation condition setting unit 51.

The irradiation condition setting unit 51 performs correction corresponding to the radiation tube 27 whose focus has been selected as the pre-imaging focus FP for the projection image obtained from the radiation detector 26 in the pre-imaging in order to absorb the individual difference between the focuses F1 to F14 of the radiation tubes 27. Then, the irradiation condition setting unit 51 analyzes the corrected projection image and sets the irradiation conditions of the radiation 37 in the tomosynthesis imaging. The irradiation condition setting unit 51 outputs the set irradiation conditions to the tomosynthesis imaging control unit 50B.

The irradiation conditions include a tube voltage applied to the radiation tube 27, a tube current, and the time for which the radiation 37 is emitted. An example of the setting of the irradiation conditions is increasing the tube voltage to a rated value in a case in which the thickness of the breast M is relatively large and the density of the projection image from the radiation detector 26 is lower than a desired level. In a case in which the irradiation conditions are set on the basis of the pre-imaging, the density of the projection image captured by the tomosynthesis imaging and the density of the tomographic image T generated from the projection image are at a substantially constant level regardless of an individual difference in the breast M. In addition, instead of the tube current and the irradiation time, a tube current-irradiation time product (a so-called mAs value) may be used as the irradiation conditions.

The tomosynthesis imaging control unit 50B performs the tomosynthesis imaging illustrated in FIG. 7 using the plurality of focuses F1 to F14 including the pre-imaging focus FP. Specifically, the tomosynthesis imaging control unit 50B drives the plurality of radiation tubes 27 under the irradiation conditions set by the irradiation condition setting unit 51 such that the plurality of radiation tubes 27 sequentially emit the radiation 37 to the breast M from the focuses F1 to F14. Then, a plurality of projection images detected by the radiation detector 26 are output from the radiation detector 26 to the tomographic image generation unit 52.

As illustrated in FIG. 8, the tomographic image generation unit 52 generates tomographic images T on the basis of the plurality of projection images from the radiation detector 26. The tomographic image generation unit 52 transmits the generated tomographic images T to the image DB server 14 through the network 13.

In FIG. 9, the irradiation field limiter 40 is not illustrated for simplicity of illustration. The pre-imaging control unit 50A and the tomosynthesis imaging control unit 50B also control the operation of the irradiation field limiter 40. Specifically, the pre-imaging control unit 50A and the tomosynthesis imaging control unit 50B move the irradiation field limiter 40 to a position immediately below a radiation tube 27 that emits the radiation 37 among the plurality of radiation tubes 27 and move the shielding plate 41 in order to set the irradiation field.

Figure 10:
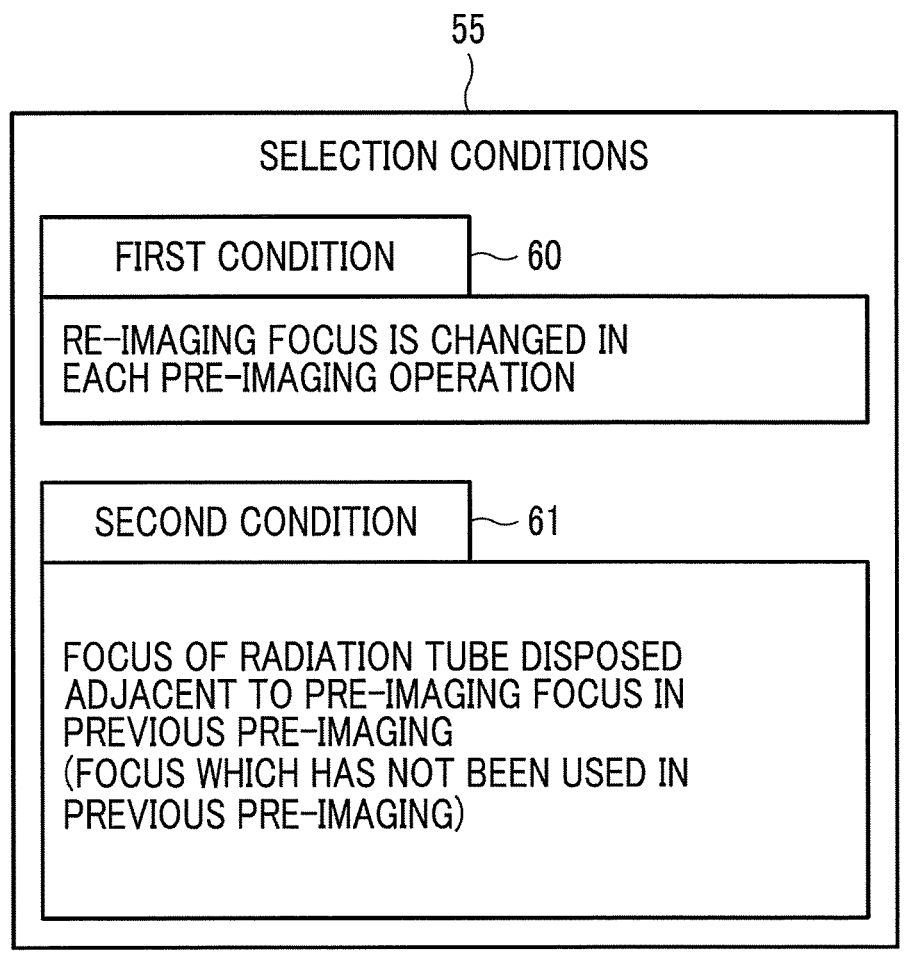
FIG. 10 is a diagram illustrating selection conditions.

As illustrated in FIG. 10, the selection conditions 55 include a first condition 60 and a second condition 61. The first condition 60 defines the time when the pre-imaging focus FP is changed. The second condition 61 defines which of the plurality of focuses F is selected as the pre-imaging focus FP.

FIG. 10 illustrates the first condition 60 in which the pre-imaging focus FP is changed in each pre-imaging operation. In addition, FIG. 10 illustrates the second condition 61 in which the focus F of a radiation tube 27 disposed adjacent to the radiation tube 27 whose focus has been used as the pre-imaging focus FP in the previous pre-imaging is selected as the pre-imaging focus FP in the next pre-imaging. The second condition 61 is an example of the second condition in which a focus that has not been used as the pre-imaging focus FP in the previous pre-imaging is selected as the pre-imaging focus FP in the next pre-imaging.

Figure 11:
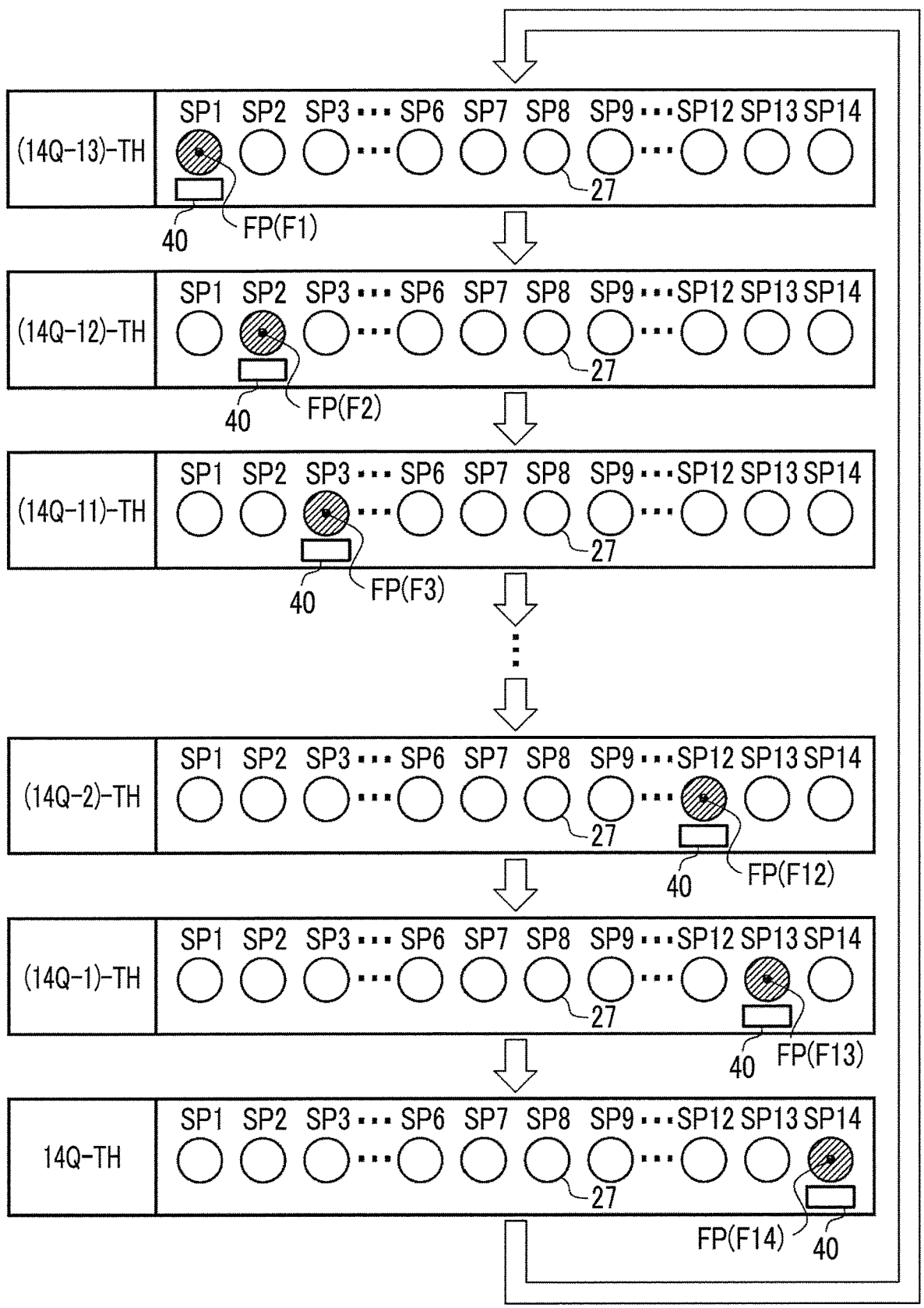
FIG. 11 is a diagram illustrating the change of a pre-imaging focus in the case of the selection conditions illustrated in FIG. 10.

In the case of the selection conditions 55 illustrated in FIG. 10, for example, the pre-imaging focus FP selected by the pre-imaging control unit 50A is changed as illustrated in FIG. 11. That is, in a (14Q-13)-th (Q is a natural number equal to or greater than 1) pre-imaging operation, the focus F1 of the radiation tube 27 disposed at the position SP1 is used as the pre-imaging focus FP. In addition, in a (14Q-12)-th pre-imaging operation, the focus F2 of the radiation tube 27 disposed at the position SP2 is used as the pre-imaging focus FP. Similarly, in a (14Q-11)-th pre-imaging operation, the focus F3 of the radiation tube 27 disposed at the position SP3 is used as the pre-imaging focus FP. In a (14Q-1)-th pre-imaging operation, the focus F13 of the radiation tube 27 disposed at the position SP13 is used as the pre-imaging focus FP. In a (14Q)-th pre-imaging operation, the focus F14 of the radiation tube 27 disposed at the position SP14 is used as the pre-imaging focus FP.

The "adjacent positions" include literally adjacent positions, such as the positions SP1 and SP2 or the positions SP3 and SP4, and substantially adjacent positions, such as the positions SP1 and SP14, which are not literally adjacent positions, but are considered to be adjacent to each other from the arrangement relationship between the plurality of focuses F1 to F14, as illustrated in the example of FIG. 11.

The pre-imaging control unit 50A changes the movement position of the irradiation field limiter 40 according to the position of the pre-imaging focus FP and directs the irradiation field limiter 40 to set the irradiation field whenever the movement position is changed.

Here, according to the second condition 61 illustrated in FIG. 10, as illustrated in FIG. 11, the pre-imaging focus FP in the next pre-imaging is known before the next pre-imaging starts. Therefore, before the next pre-imaging starts, the pre-imaging control unit 50A moves the irradiation field limiter 40 to the position of the pre-imaging focus FP in the next pre-imaging to set the irradiation field.

Figure 12:
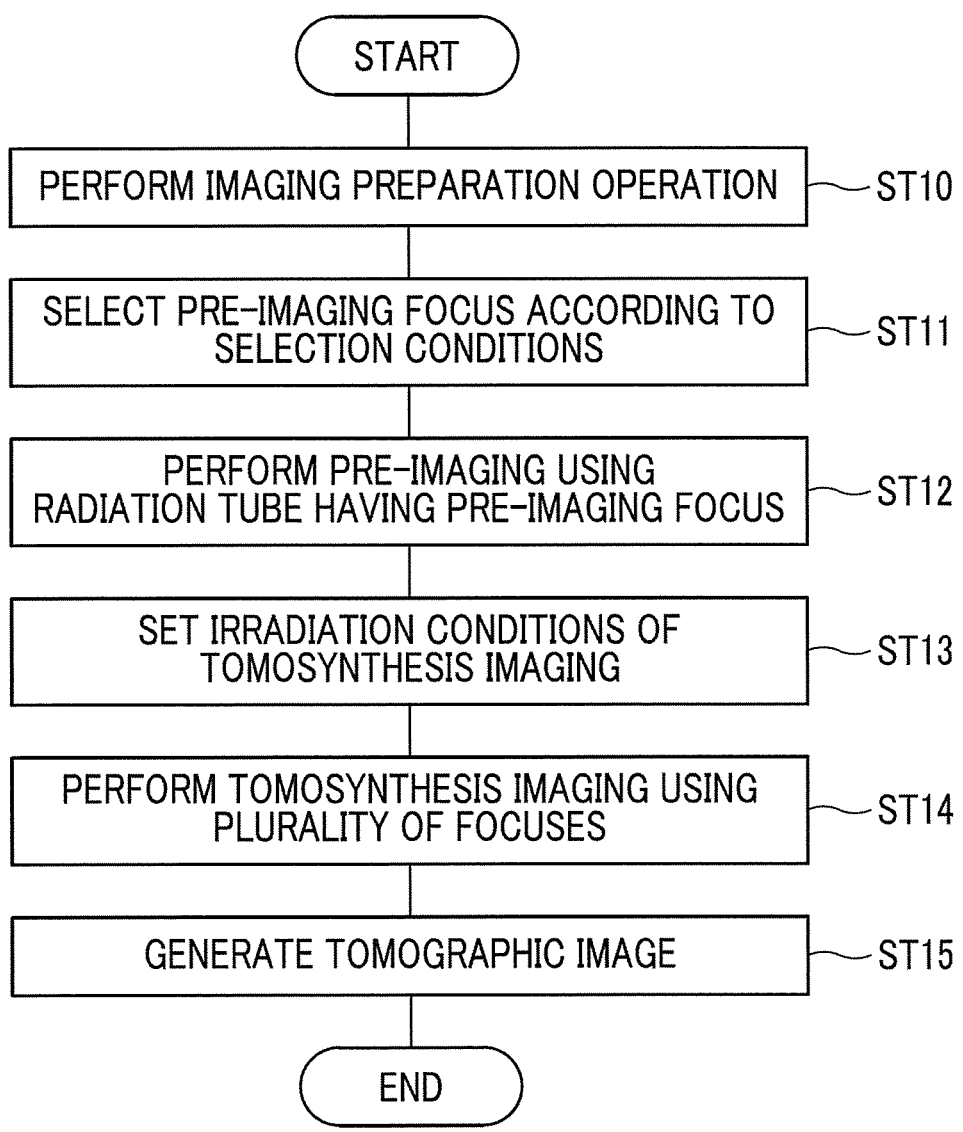
FIG. 12 is a flowchart illustrating the procedure of tomosynthesis imaging by the mammography apparatus.

Next, the operation of the above-mentioned configuration will be described with reference to a flowchart illustrated in FIG. 12. The procedure of the tomosynthesis imaging by the mammography apparatus 10 starts from an imaging preparation operation in Step ST10. The imaging preparation operation is performed by a radiology technician who operates the mammography apparatus 10 and is mainly related to the positioning of the breast M. For example, the imaging preparation operation includes an operation which guides the subject H to the apparatus main body 11 such that the breast M is placed on the detector accommodation portion 23, moves the compression plate 29 to the detector accommodation portion 23, and compresses the breast M interposed between the compression plate 29 and the detector accommodation portion 23. After the imaging preparation operation ends, the radiology technician inputs a command to start tomosynthesis imaging.

Before the tomosynthesis imaging, as illustrated in Step ST11, the pre-imaging control unit 50A selects one focus F as the pre-imaging focus FP from the plurality of focuses F1 to F14 according to the selection conditions 55. Then, as illustrated in Step ST12, the pre-imaging control unit 50A performs pre-imaging using the pre-imaging focus FP (pre-imaging control step).

For example, as illustrated in FIG. 10, the selection conditions 55 includes the first condition 60 in which the pre-imaging focus FP is changed in each pre-imaging operation and the second condition 61 in which the focus F of a radiation tube 27 disposed adjacent to the radiation tube 27 whose focus has been used as the pre-imaging focus FP in the previous pre-imaging is selected as the pre-imaging focus FP in the next pre-imaging. In the case of the selection conditions 55, as illustrated in FIG. 11, the pre-imaging focus FP is changed in each pre-imaging operation and the focus F of a radiation tube 27 disposed adjacent to the radiation tube 27 whose focus has been used as the pre-imaging focus FP in the previous pre-imaging is selected.

As such, the pre-imaging is performed using one pre-imaging focus FP selected from the plurality of focuses F1 to F14 according to the selection conditions 55 preset in order to prevent the concentration of load on one focus F. Therefore, a situation does not occur in which load is concentrated on one focus F used for both pre-imaging and tomosynthesis imaging and the deterioration of the performance of the one focus F is faster than that of other focuses F as in a case in which one of the plurality of focuses F is used for both pre-imaging and tomosynthesis imaging.

It is considered that a focus F only for pre-imaging is provided separately from the plurality of focuses F. However, in this case, there is a concern that the part cost and size of the radiation source 25 will be increased by a value corresponding to the focus F only for pre-imaging. In contrast, in this embodiment, the focus F only for pre-imaging is not provided and one of the plurality of focuses F is used as the pre-imaging focus FP. Therefore, it is possible to eliminate the concern that the part cost and size of the radiation source 25 will increase.

In a case in which the first condition 60 indicates that the pre-imaging focus FP is changed in each pre-imaging operation, it is possible to more effectively prevent the concentration of load on one focus F. In a case in which the second condition 61 indicates that the focus F which has not been used as the pre-imaging focus FP in the previous pre-imaging is selected as the pre-imaging focus FP in the next pre-imaging, the same effect as described above is obtained. In other words, selecting the focus F which has not been used as the pre-imaging focus FP in the previous pre-imaging as the pre-imaging focus FP in the next pre-imaging means that any focus F other than the pre-imaging focus FP used in the previous pre-imaging may be selected.

In a case in which the second condition 61 indicates that the focus F of a radiation tube 27 disposed adjacent to the radiation tube 27 whose focus has been used as the pre-imaging focus FP in the previous pre-imaging is selected as the pre-imaging focus FP in the next pre-imaging, the following effect is obtained. That is, the process performed by the pre-imaging control unit 50A is simpler than that in a case in which the pre-imaging focus FP is selected without any restriction.

The number of irradiation field limiters 40 provided is less than the number of focuses F. Therefore, it is possible to reduce a part cost. In addition, before the pre-imaging control unit 50A starts the next pre-imaging, the irradiation field limiter 40 is moved to the position of the pre-imaging focus FP in the next pre-imaging to set the irradiation field. Therefore, the pre-imaging time can be shorter than that in a case in which the irradiation field limiter 40 is moved to set the irradiation field after the next pre-imaging starts.

The projection image output from the radiation detector 26 in the pre-imaging is output to the irradiation condition setting unit 51. The irradiation condition setting unit 51 sets the irradiation conditions of the radiation 37 in the tomosynthesis imaging on the basis of the projection image from the radiation detector 26 (Step ST13). The set irradiation conditions are output from the irradiation condition setting unit 51 to the tomosynthesis imaging control unit 50B.

Then, as illustrated in Step ST14, the tomosynthesis imaging control unit 50B performs the tomosynthesis imaging illustrated in FIG. 7 using the plurality of focuses F1 to F14 including the pre-imaging focus FP (tomosynthesis imaging control step).

In the radiation tubes 27, the focuses F1 to F14 of the radiation 37 are disposed at the plurality of positions SP1 to SP14 which are set so as to be linearly arranged at equal intervals D. Since the regularity of the arrangement positions SP1 to SP14 of the focuses F1 to F14 is ensured, it is possible to simplify the process related to the generation of the tomographic image T.

As illustrated in FIG. 3, the radiation tube 27 includes the field-emission-type cathode 35 and the anode 36 which is a fixed anode. The field-emission-type cathode 35 generates a much smaller amount of heat than a cathode with a filament structure which emits thermal electrons. Therefore, a heat dissipation structure is unnecessary and it is possible to reduce the size of the radiation tube. In addition, the fixed anode does not require a rotating mechanism unlike a rotating anode and it is also possible to reduce the size of the radiation tube. Therefore, a larger number of radiation tubes 27 can be disposed in a limited space of the housing 28. In a case in which a larger number of radiation tubes 27 can be disposed, it is possible to obtain a larger number of projection images in the tomosynthesis imaging. Therefore, the amount of image information used to generate the tomographic image T increases, which makes it possible to improve the quality of the tomographic image T.

The projection image output from the radiation detector 26 in the tomosynthesis imaging is output to the tomographic image generation unit 52. As illustrated in FIG. 8, the tomographic image generation unit 52 generates the tomographic image T on the basis of the projection image from the radiation detector 26 (Step ST15). The generated tomographic image T is transmitted from the tomographic image generation unit 52 to the image DB server 14.

Second Embodiment

Figure 13:
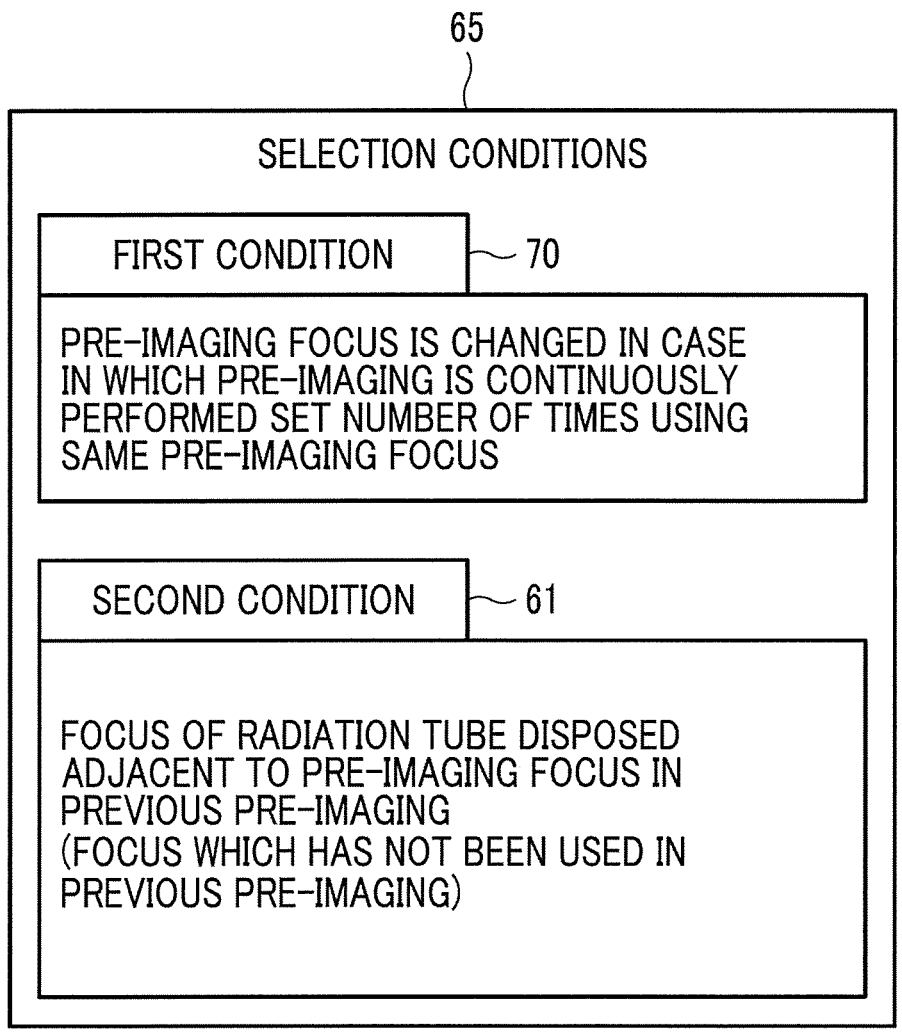
FIG. 13 is a diagram illustrating selection conditions according to a second embodiment.

In a second embodiment illustrated in FIG. 13, the pre-imaging focus FP is changed in a case in which pre-imaging is continuously performed a set number of times using the same pre-imaging focus FP.

In FIG. 13, selection conditions 65 according to the second embodiment include a first condition 70 in which the pre-imaging focus FP is changed in a case in which the pre-imaging is continuously performed a set number of times using the same pre-imaging focus FP and a second condition 61 that is the same as that in the first embodiment. The set number of times is two or more and is, for example, five.

In this case, the pre-imaging control unit 50A counts the number of pre-imaging operations performed using the same pre-imaging focus FP. In a case in which the count number is equal to the set number of times, the pre-imaging control unit 50A changes the pre-imaging focus FP to the focus F of the radiation tube 27 disposed adjacent to the radiation tube 27 whose focus has been used as the pre-imaging focus FP in the previous pre-imaging.

As such, in the second embodiment, the first condition 70 in which the pre-imaging focus FP is changed in a case in which pre-imaging is continuously performed a set number of times using the same pre-imaging focus FP is used. Therefore, it is not necessary to change the content of correction for absorbing the individual difference between the focuses F1 to F14 of the radiation tubes 27, which is performed for the projection image in the irradiation condition setting unit 51, in each pre-imaging operation.

Third Embodiment

Figure 14:
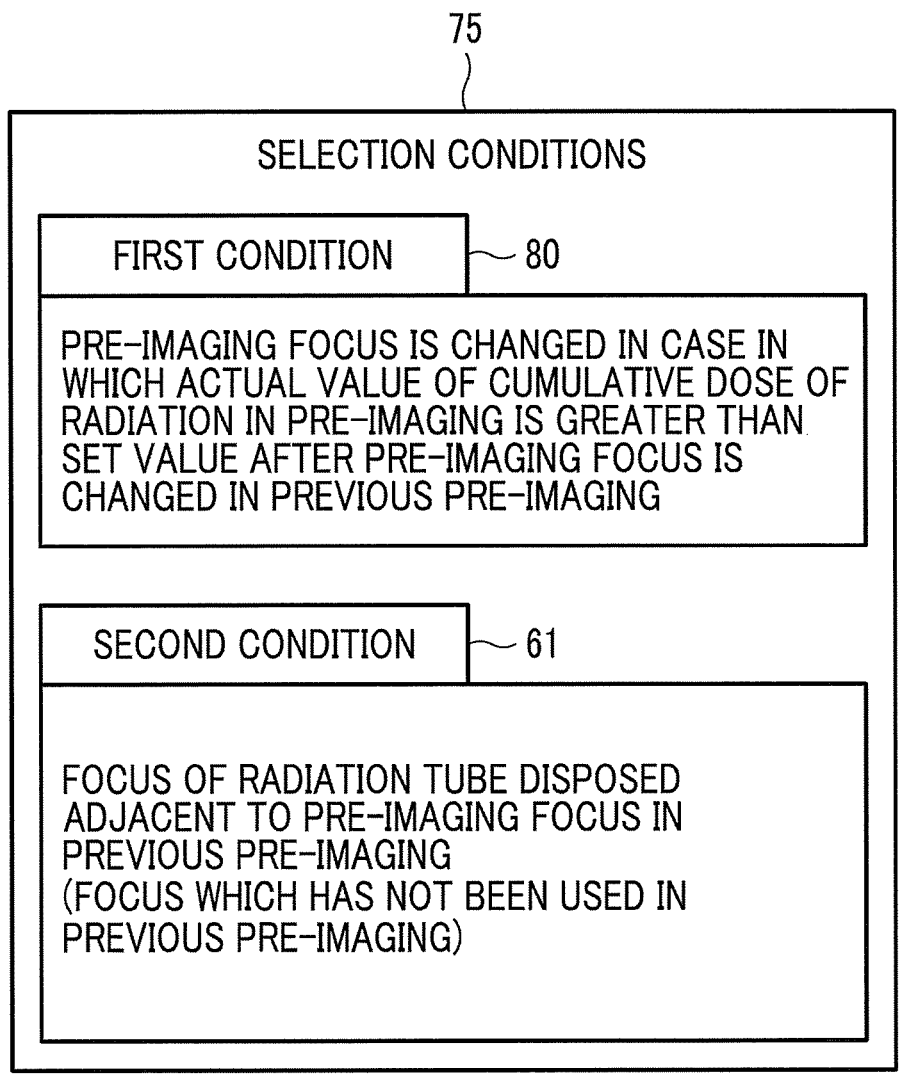
FIG. 14 is a diagram illustrating selection conditions according to a third embodiment.

In a third embodiment illustrated in FIG. 14, the pre-imaging focus FP is changed in a case in which an actual value of the cumulative dose of the radiation 37 in the pre-imaging is greater than a set value after the pre-imaging focus FP is changed in the previous pre-imaging.

In FIG. 14, selection conditions 75 according to the third embodiment include a first condition 80 in which the pre-imaging focus FP is changed in a case in which the actual value of the cumulative dose of the radiation 37 in the pre-imaging is greater than the set value after the pre-imaging focus FP is changed in the previous pre-imaging and a second condition 61 that is the same as that in the first embodiment. The actual value of the cumulative dose is, for example, a cumulative irradiation time or a cumulative tube current-irradiation time product. The dose of the radiation 37 may be actually measured by a dosimeter and the cumulative dose may be used as the actual value. The set value is the actual value of the cumulative dose in a case in which the pre-imaging is performed a plurality of times, for example, five times under the preset irradiation conditions.

In this case, the pre-imaging control unit 50A stores the actual values of the doses of the radiation 37 in each pre-imaging operation. Then, the pre-imaging control unit 50A adds the stored actual values to calculate the actual value of the cumulative dose after the pre-imaging focus FP is changed in the previous pre-imaging. In a case in which the calculated actual value of the cumulative dose is greater than the set value, the pre-imaging control unit 50A changes the pre-imaging focus FP to the focus of the radiation tube 27 disposed adjacent to the radiation tube 27 whose focus has been used as the pre-imaging focus FP in the previous pre-imaging.

As such, in the third embodiment, the first condition 80 in which the pre-imaging focus FP is changed in a case in which the actual value of the cumulative dose of the radiation 37 in the pre-imaging is greater than the set value after the pre-imaging focus FP is changed in the previous pre-imaging is used. Therefore, similarly to the second embodiment, it is not necessary to change the content of correction for absorbing the individual difference between the focuses F1 to F14 of the radiation tubes 27, which is performed for the projection image in the irradiation condition setting unit 51, in each pre-imaging operation.

Fourth Embodiment

Figure 15:
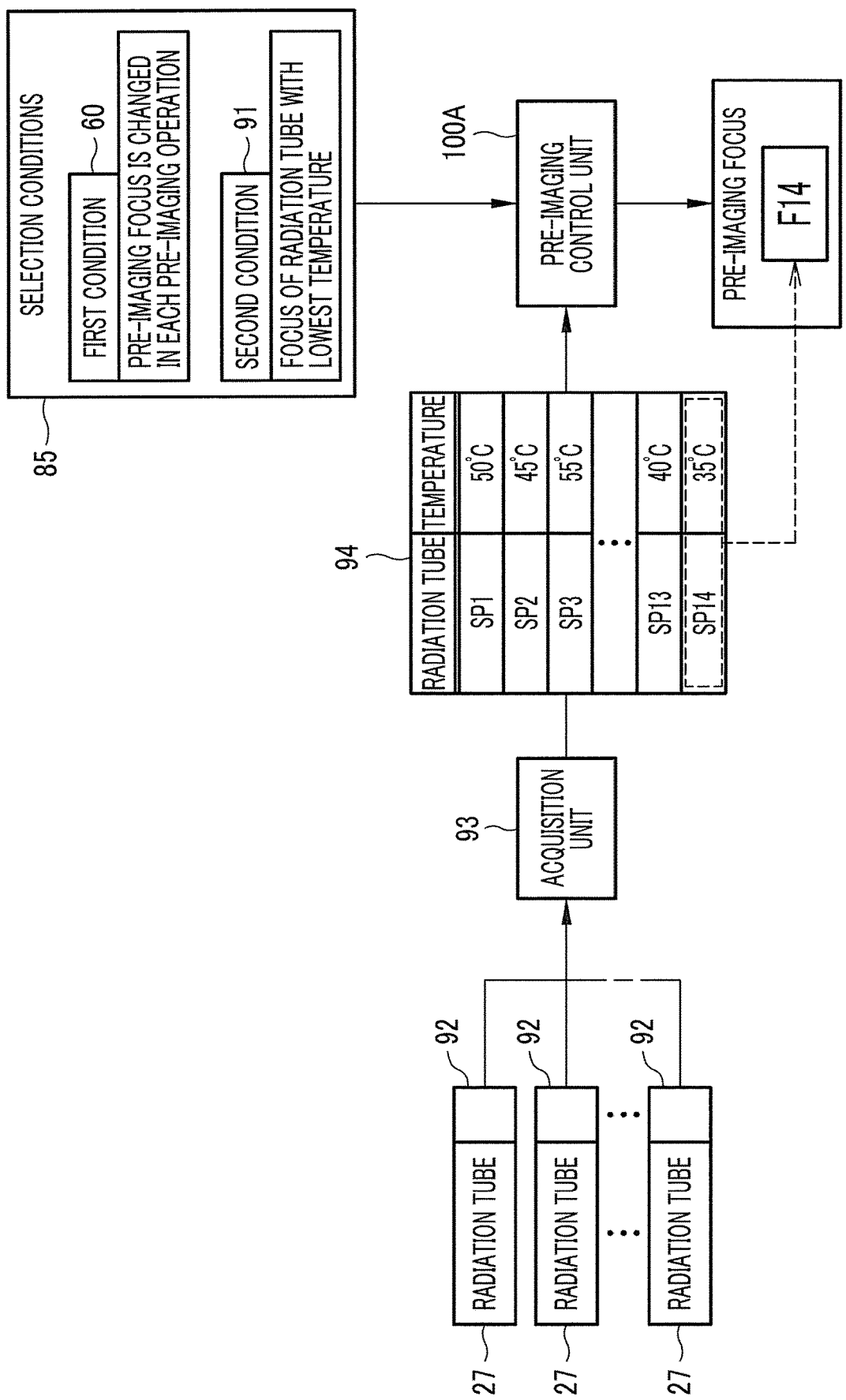
FIG. 15 is a diagram illustrating a fourth embodiment in which the temperature of each of a plurality of radiation tubes is acquired and a focus of a radiation tube with the lowest temperature is selected as the pre-imaging focus in the next pre-imaging.

In a fourth embodiment illustrated in FIG. 15, the temperature of each of a plurality of radiation tubes 27 is acquired and the focus F of a radiation tube 27 with the lowest temperature is selected as the pre-imaging focus FP in the next pre-imaging.

In FIG. 15, selection conditions 85 according to the fourth embodiment include a first condition 60 that is the same as that in the first embodiment and a second condition 91 in which the focus F of the radiation tube 27 with the lowest temperature is selected as the pre-imaging focus FP in the next pre-imaging.

A temperature sensor 92 that measures temperature is attached to each radiation tube 27. In addition, the control device comprises an acquisition unit 93 that acquires the temperature of each of the plurality of radiation tubes 27 measured by the temperature sensors 92. The acquisition unit 93 outputs the temperature of each of the plurality of radiation tubes 27 acquired as illustrated in a table 94 to a pre-imaging control unit 100A.

The pre-imaging control unit 100A selects the focus F of the radiation tube 27 with the lowest temperature as the pre-imaging focus FP according to the second condition 91. FIG. 15 illustrates an example in which the radiation tube 27 with the lowest temperature is the radiation tube 27 (temperature 35° C.) disposed at the position SP14 and the pre-imaging control unit 100A selects the focus F14 of the radiation tube 27 disposed at the position SP14 as the pre-imaging focus FP.

As such, in the fourth embodiment, the acquisition unit 93 acquires the temperature of each of the plurality of radiation tubes 27. Then, the second condition 91 in which the focus F of the radiation tube 27 with the lowest temperature is selected the pre-imaging focus FP in the next pre-imaging is used. A radiation tube 27 with relatively high temperature is likely to have been used recently. Therefore, the focus F of the radiation tube 27 which has relatively high temperature and is likely to have been used recently is selected as the pre-imaging focus FP to prevent the situation in which the deterioration of the performance of the radiation tube 27 is accelerated. In addition, it is possible to remove a part with extremely high temperature which causes the deterioration of the performance of the radiation tube 27.

Further, instead of the first condition 60, the first condition 70 according to the second embodiment illustrated in FIG. 13 or the first condition 80 according to the third embodiment illustrated in FIG. 14 may be used. In addition, instead of measuring the temperature with the temperature sensor 92, the temperature may be estimated from the outside air temperature or the irradiation history of each radiation tube 27 and the acquisition unit 93 may acquire the estimated temperature.

Fifth Embodiment

Figure 16:
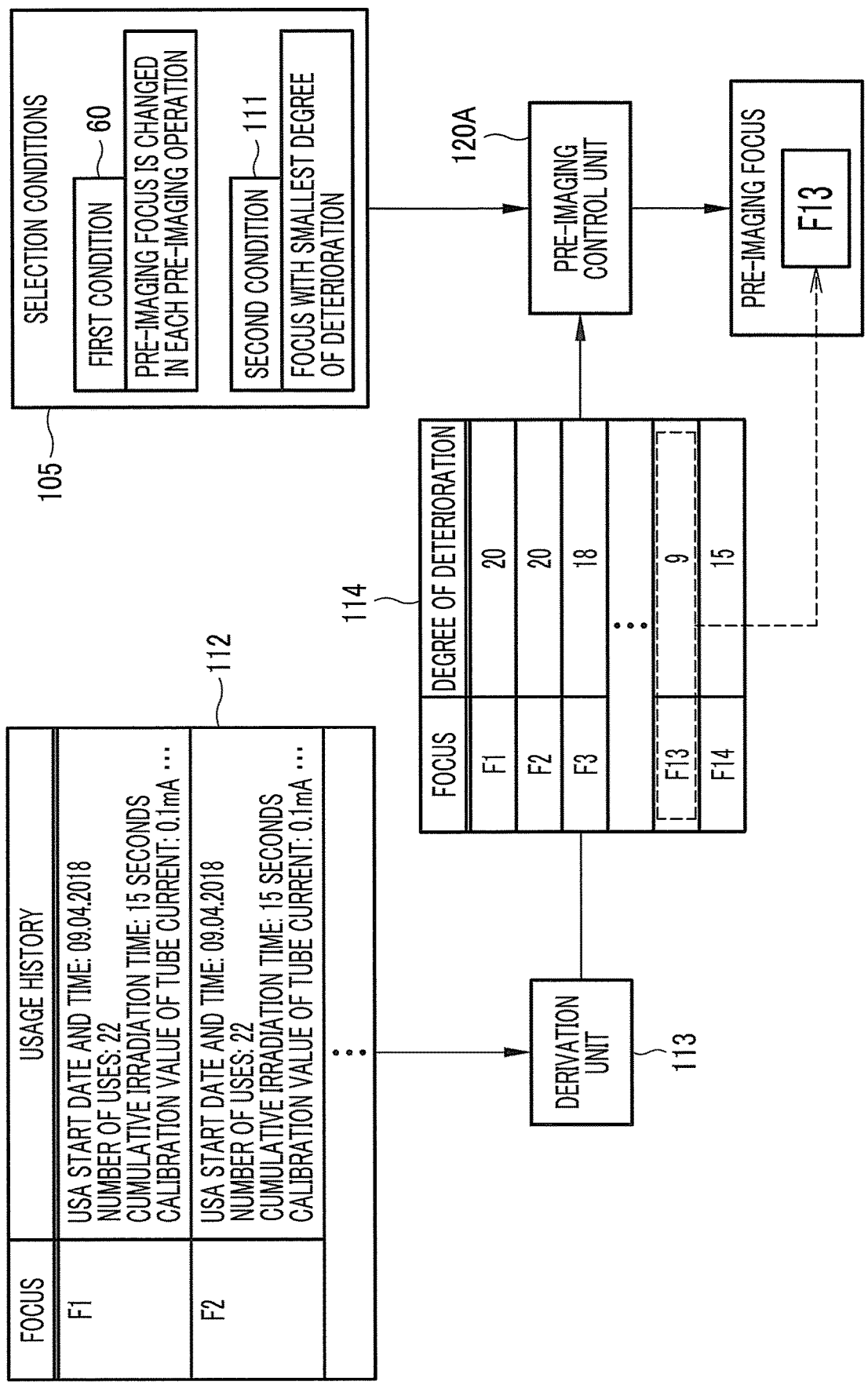
FIG. 16 is a diagram illustrating a fifth embodiment in which the degree of deterioration of the performance of each of a plurality of focuses is derived and a focus with the smallest degree of deterioration is selected as the pre-imaging focus in the next pre-imaging.

In a fifth embodiment illustrated in FIG. 16, the degree of deterioration of the performance of each of the plurality of focuses F1 to F14 is derived on the basis of the usage history of each of the plurality of focuses F1 to F14. Then, a focus F with the smallest degree of deterioration is selected as the pre-imaging focus FP in the next pre-imaging.

In FIG. 16, the selection conditions 105 according to the fifth embodiment includes a first condition 60 that is the same as that in the first embodiment and a second condition 111 in which a focus F with the smallest degree of deterioration is set as the pre-imaging focus FP in the next pre-imaging.

The control device stores usage history information 112 in which the usage history of each of the plurality of focuses F1 to F14 has been registered in, for example, the storage device 53. In addition, the control device comprises a derivation unit 113 that derives the degree of deterioration of the performance of each of the plurality of focuses F1 to F14 on the basis of the usage history of the usage history information 112. The usage history is, for example, a use start date and time, the number of times the focus is used, a cumulative irradiation time, and a calibration value of a tube current. The calibration value of the tube current is added to the tube current of the irradiation conditions in order to compensate for a reduction in the value of the tube current required to emit a specified amount of radiation at a specified tube voltage with the deterioration of the performance. The derivation unit 113 calculates an expression having a plurality of types of usage histories as parameters to derive the degree of deterioration. The derivation unit 113 outputs the degree of deterioration of each of the plurality of focuses F1 to F14 derived as illustrated in a table 114 to a pre-imaging control unit 120A.

The pre-imaging control unit 120A selects a focus F with the smallest degree of deterioration as the pre-imaging focus FP according to the second condition 111. FIG. 16 illustrates an example in which the focus F with the smallest degree of deterioration is the focus F13 (the degree of deterioration is 9) of the radiation tube 27 disposed at the position SP13 and the pre-imaging control unit 120A selects the focus F13 of the radiation tube 27 disposed at the position SP13 as the pre-imaging focus FP.

As such, in the fifth embodiment, the derivation unit 113 derives the degree of deterioration of the performance of each of the plurality of focuses F1 to F14. Then, the second condition 111 in which a focus F with the smallest degree of deterioration is set as the pre-imaging focus FP in the next pre-imaging is used. Therefore, as a result, it is possible to equalize the degrees of deterioration of the performance of the focuses F1 to F14 and to more effectively prevent the concentration of load on one focus F.

According to the second condition 111, in a case in which there is a newly replaced radiation tube 27 among the plurality of radiation tubes 27, the focus F of the newly replaced radiation tube 27 is certainly selected as the pre-imaging focus FP. In a case in which the focus F of the newly replaced radiation tube 27 is selected as the pre-imaging focus FP and the irradiation condition setting unit 51 sets the irradiation conditions, it is not necessary to correct the projection image in consideration of the degree of deterioration of the performance. Therefore, the effect of simplifying the setting of the irradiation conditions is obtained.

In this case, similarly to the fourth embodiment, instead of the first condition 60, the first condition 70 according to the second embodiment illustrated in FIG. 13 or the first condition 80 according to the third embodiment illustrated in FIG. 14 may be used.

Sixth Embodiment

A sixth embodiment illustrated in FIGS. 17 to 20, the pre-imaging focus FP is changed according to a tomosynthesis imaging method.

Figure 17:
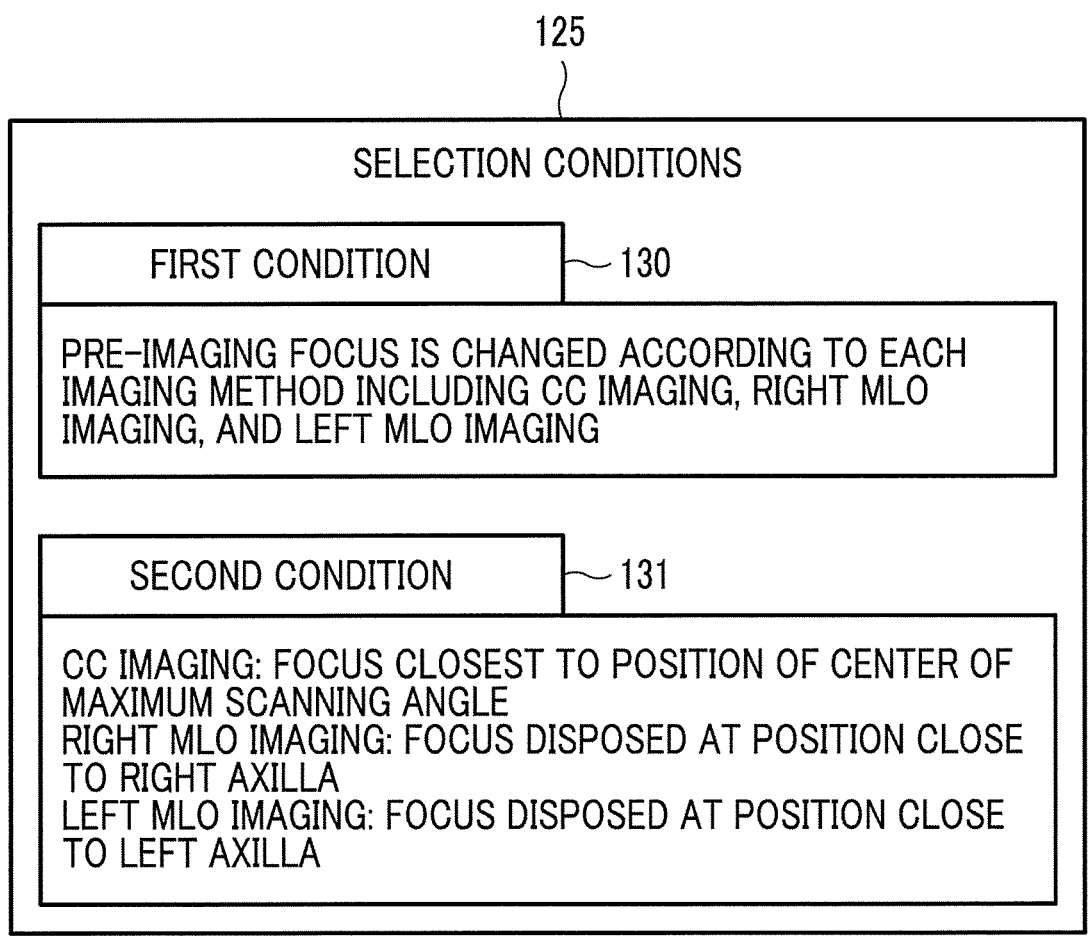
FIG. 17 is a diagram illustrating selection conditions according to a sixth embodiment.

In FIG. 17, selection conditions 125 according to the sixth embodiment include a first condition 130 and a second condition 131. The first condition 130 indicates that the pre-imaging focus FP is changed according to each imaging method including CC imaging, right MLO imaging using the right breast M as the object, and left MLO imaging using the left breast M as the object. The second condition 131 indicates that a focus F closest to the position of the center of the maximum scanning angle ψ is selected as the pre-imaging focus FP in the case of the CC imaging, a focus F that is disposed at a position close to the right axilla AP_R (see FIG. 19) of the positions at both ends is selected as the pre-imaging focus FP in the case of the right MLO imaging, and a focus F that is disposed at a position close to left axilla AP_L (see FIG. 20) of the positions at both ends is selected as the pre-imaging focus FP in the case of the left MLO imaging.

Figure 18:
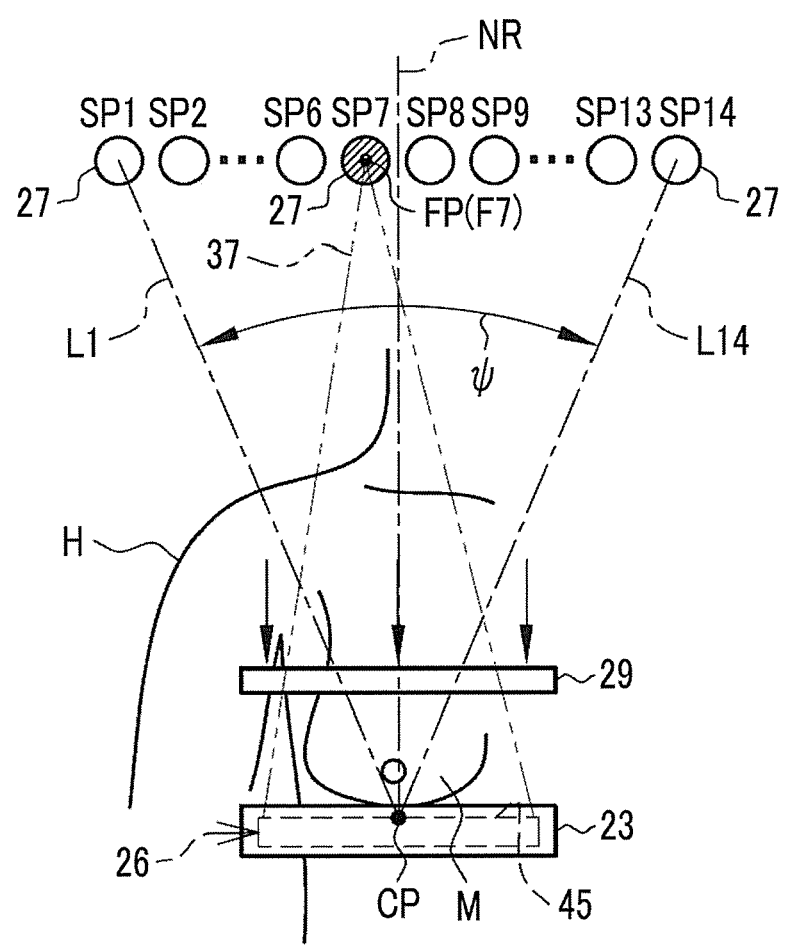
FIG. 18 is a diagram illustrating an aspect of pre-imaging in the case of a CC imaging method.
Figure 19:
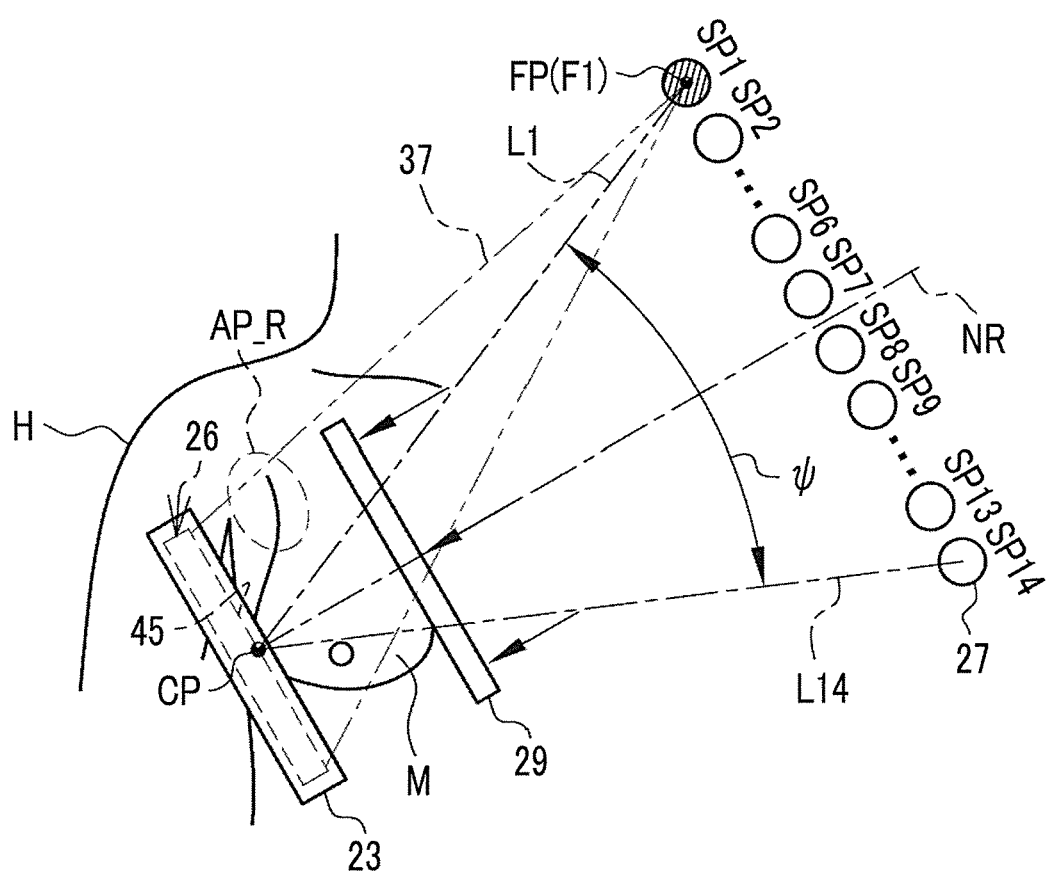
FIG. 19 is a diagram illustrating an aspect of pre-imaging in the case of a right MLO imaging method.
Figure 20:
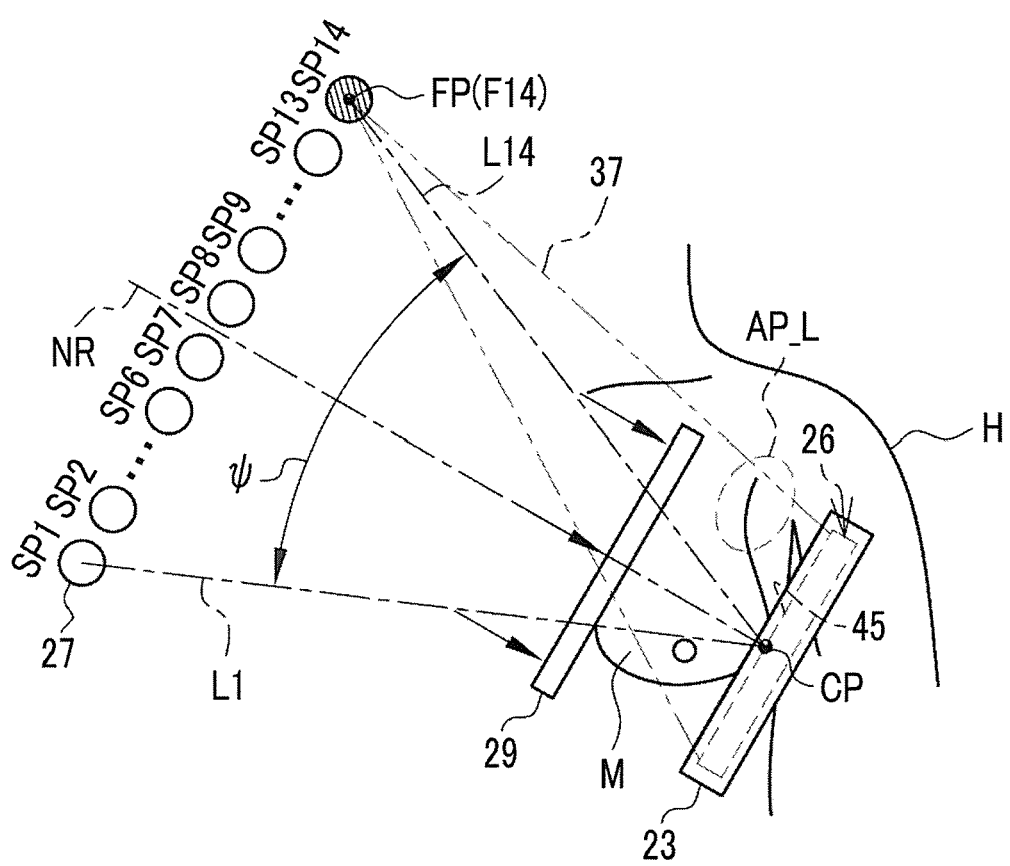
FIG. 20 is a diagram illustrating an aspect of pre-imaging in the case of a left MLO imaging method.

In the case of the selection conditions 125, specifically, the pre-imaging focus FP is as illustrated in FIGS. 18 to 20. That is, in the CC imaging, as illustrated in FIG. 18, the focus F7 of the radiation tube 27 disposed at the position SP7 which is the radiation tube 27 closest to the position of the center of the maximum scanning angle ψ is selected as the pre-imaging focus FP. Instead of the focus F7, the focus F8 of the radiation tube 27 disposed at the position SP8 may be selected as the pre-imaging focus FP.

In the right MLO imaging, as illustrated in FIG. 19, the focus F1 of the radiation tube 27 disposed at the position SP1 which is the radiation tube 27 disposed at a position close to the right axilla AP_R is selected as the pre-imaging focus FP. In the left MLO imaging, as illustrated in FIG. 20, the focus F14 of the radiation tube 27 disposed at the position SP14 which is the radiation tube 27 disposed at a position close to the left axilla AP_L is selected as the pre-imaging focus FP.

In the CC imaging, since most of the object is the breast M, there is relatively little bias in the composition of the object. Therefore, in the case of the CC imaging, it is preferable to select, as the pre-imaging focus FP, the focus F closest to the position of the center of the maximum scanning angle ψ where there is no bias. In the MLO imaging, not only the breast M but also the axilla AP is the object. In the MLO imaging, the lymph node of the axilla AP is often a medical treatment target. Therefore, in the case of the MLO imaging, it is preferable to select, as the pre-imaging focus FP, the focus F disposed at a position close to the axilla AP. The selection conditions 125 illustrated in FIG. 17 are obtained by embodying the preferred aspect of the pre-imaging focus FP in each of the above-mentioned imaging methods.

In this example, since the focus F is not disposed at the position of the normal line NR, the focus F7 of the radiation tube 27 disposed at the position SP7 is the focus F closest to the position of the center of the maximum scanning angle ψ. However, in a case in which the focus F is disposed at the position of the normal line NR, it is natural that the focus F disposed at the position of the normal line NR is the focus F closest to the position of the center of the maximum scanning angle ψ.

Seventh Embodiment

Figure 21:
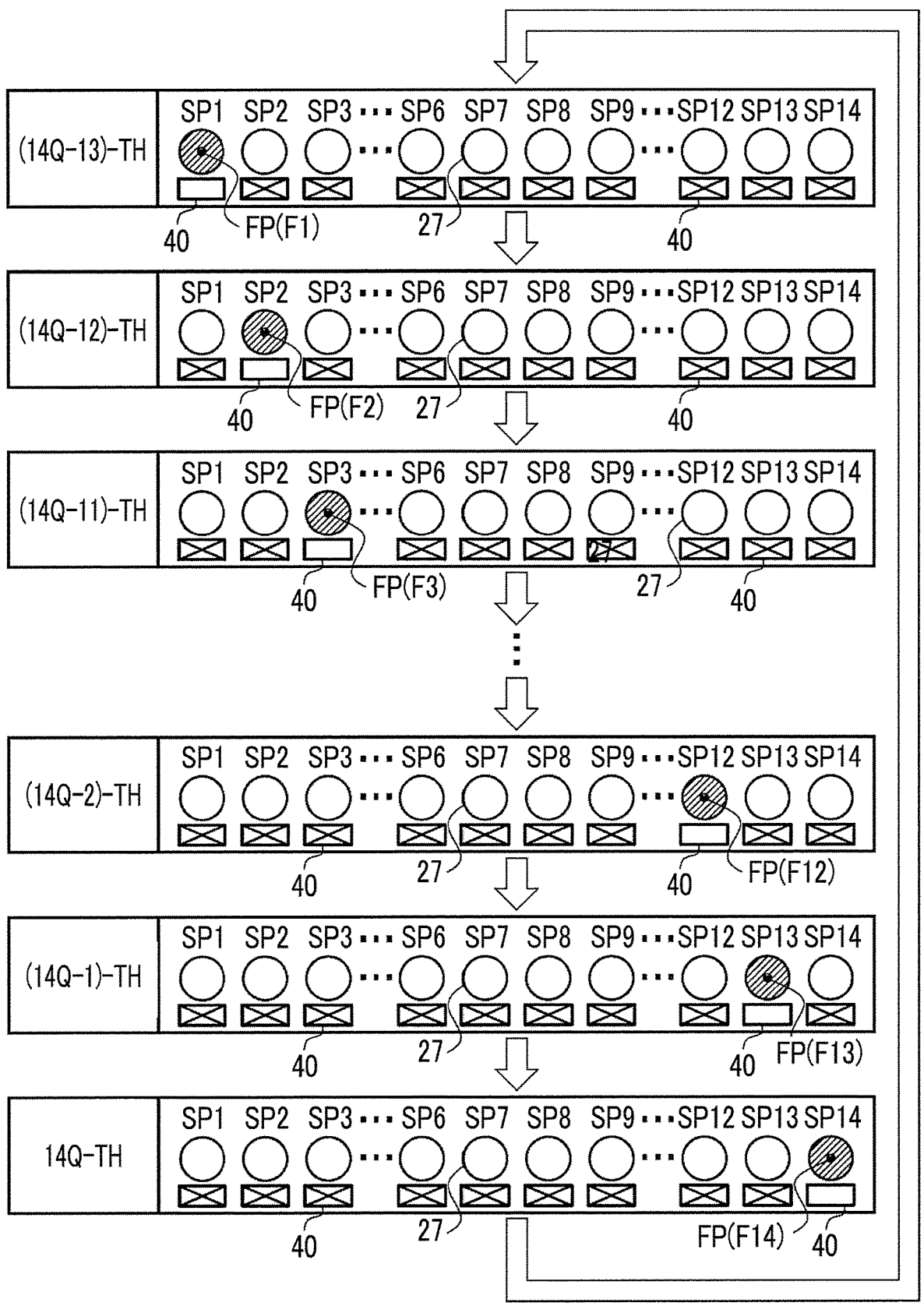
FIG. 21 is a diagram illustrating a seventh embodiment in which an irradiation field limiter is provided for each of a plurality of focuses.

In a seventh embodiment illustrated in FIG. 21, the irradiation field limiter 40 is provided for each of the plurality of focuses F1 to F14.

FIG. 21 illustrates an example of the change of the pre-imaging focus FP in the case of the selection conditions 55 similarly to FIG. 11 in the first embodiment. In the first embodiment, one irradiation field limiter 40 is provided. However, in FIG. 21, the irradiation field limiter 40 is provided for each of the plurality of focuses F.

In this case, the pre-imaging control unit 50A operates only the irradiation field limiter 40 corresponding to the pre-imaging focus FP to set the irradiation field. In addition, before the next pre-imaging starts, the pre-imaging control unit 50A operates the irradiation field limiter 40 corresponding to the pre-imaging focus FP in the next pre-imaging to set the irradiation field.

As such, in the seventh embodiment, the irradiation field limiter 40 is provided for each of the plurality of focuses F1 to F14. Therefore, the time and effort required to move the irradiation field limiter 40 are reduced. In addition, before the next pre-imaging starts, the pre-imaging control unit 50A operates the irradiation field limiter 40 corresponding to the pre-imaging focus FP in the next pre-imaging to set the irradiation field. Therefore, similarly to the first embodiment, the pre-imaging time can be shorter than that in the case in which the irradiation field limiter 40 is operated to set the irradiation field after the next pre-imaging starts.

Figure 22:
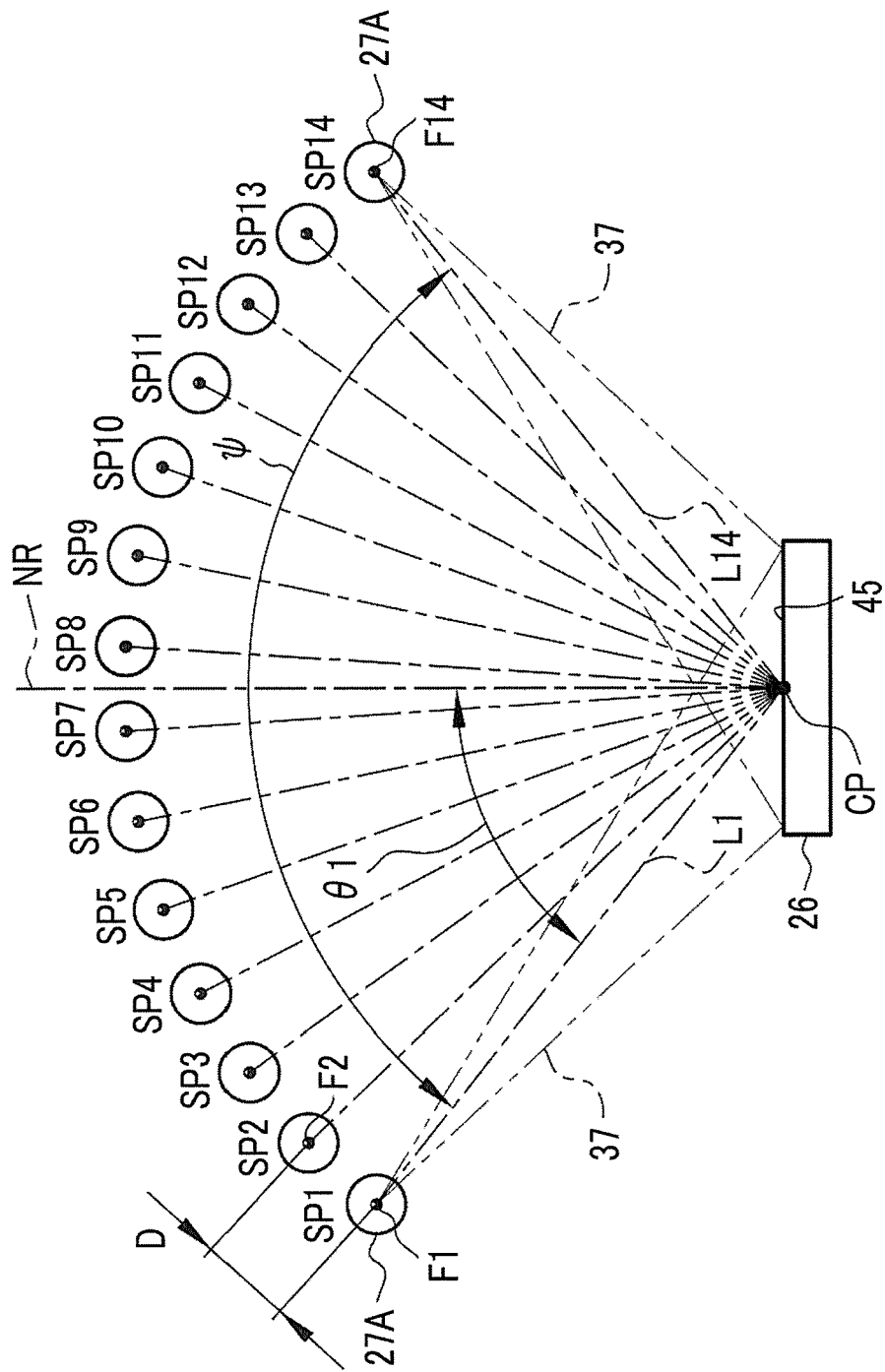
FIG. 22 is a diagram illustrating an example in which radiation tubes are disposed at a plurality of positions where the focuses of radiation are set so as to be arranged in an arc shape at equal intervals.

In each of the above-described embodiments, the positions where the focuses F are disposed are arranged in a straight line. However, the present disclosure is not limited thereto. As illustrated in FIG. 22, the plurality of positions SP1 to SP14 where the focuses F1 to F14 are disposed may be set so as to be arranged in an arc shape at equal intervals D. Even in a case in which the positions are arranged in the arc shape, the regularity of the arrangement positions SP1 to SP14 of the focuses F1 to F14 is ensured similarly to the case in which the positions are linearly arranged. Therefore, it is possible to simplify the process related to the generation of the tomographic image T.

Instead of the simple imaging in which the CC imaging illustrated in FIG. 5 and the MLO imaging illustrated in FIG. 6 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images obtained by the tomosynthesis imaging and a plurality of tomographic images T generated by the tomographic image generation unit 52.

In each of the above-described embodiments, the mammography apparatus 10 is given as an example of the tomosynthesis imaging apparatus. In the related art, performing tomosynthesis imaging in the mammography apparatus 10 has been found to be useful as a method for easily finding lesions such as microcalcifications of the breast M. Therefore, it is preferable to apply the tomosynthesis imaging apparatus according to the present disclosure to the mammography apparatus 10.

Figure 23:
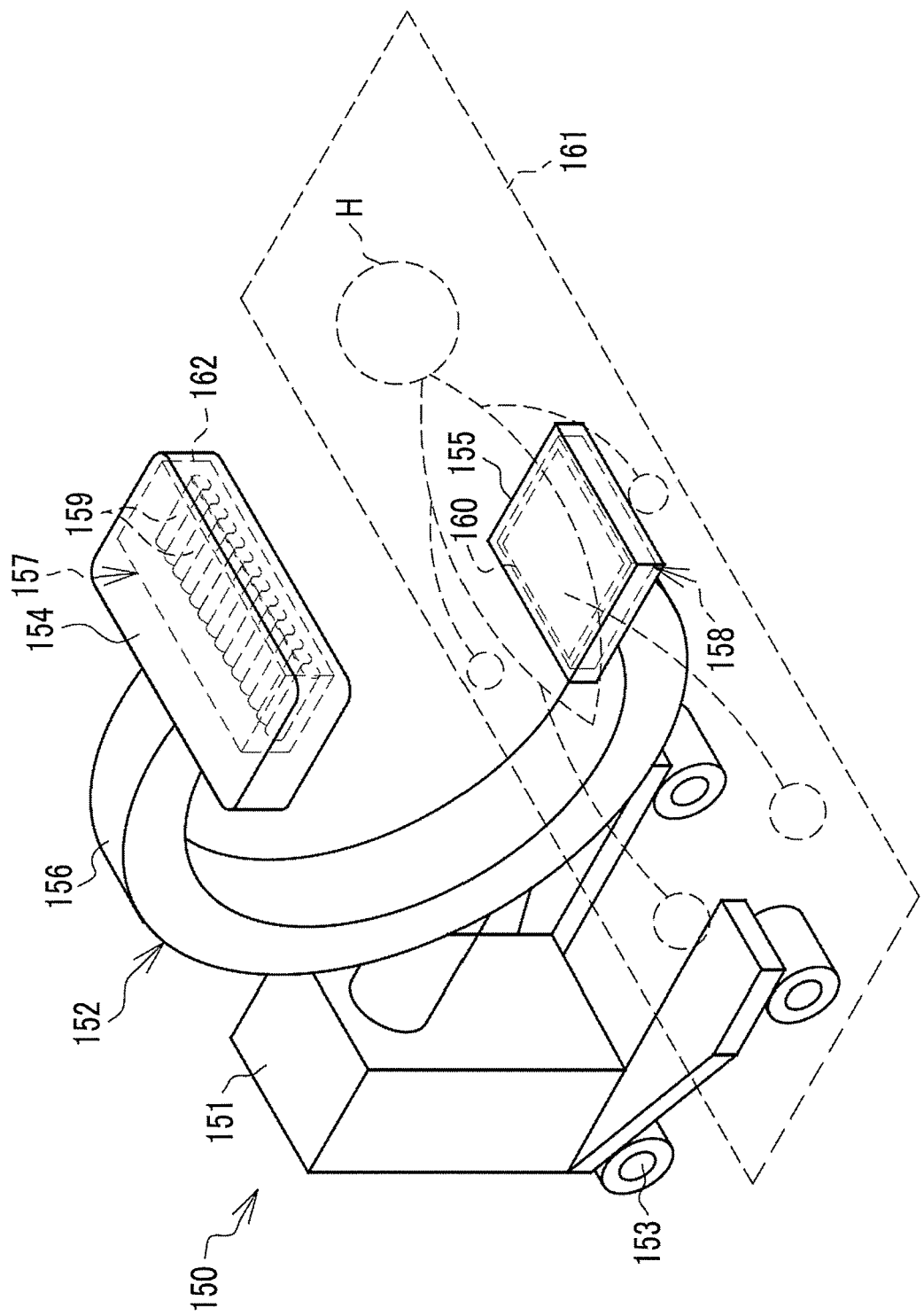
FIG. 23 is a diagram illustrating an imaging apparatus for surgery.

Of course, the tomosynthesis imaging apparatus according to the present disclosure may be applied to imaging apparatuses other than the mammography apparatus 10. For example, the tomosynthesis imaging apparatus according to the present disclosure may be applied to an imaging apparatus 150 illustrated in FIG. 23 which captures the image of the subject H during surgery.

The imaging apparatus 150 comprises an apparatus main body 151 having a control device (not illustrated) provided therein and an arm 152 having a substantially C-shape in a side view. A carriage 153 is attached to the apparatus main body 151 such that the apparatus main body 151 can be moved. The arm 152 includes a radiation source accommodation portion 154, a detector accommodation portion 155, and a main body portion 156. As in the mammography apparatus 10 illustrated in FIG. 1, the radiation source accommodation portion 154 accommodates a radiation source 157. In addition, the detector accommodation portion 155 accommodates a radiation detector 158. The radiation source accommodation portion 154 and the detector accommodation portion 155 are held by the main body portion 156 at a posture where they face each other.

The radiation source 157 and the radiation detector 158 have the same basic configurations as the radiation source 25 and the radiation detector 26 illustrated in FIG. 1, respectively. However, the imaging apparatus 150 captures an image of an object, such as the entire chest of the subject H, which is larger than the breast M. Therefore, a radiation tube 159 forming the radiation source 157 has a larger diameter than each radiation tube 27 of the mammography apparatus 10. In addition, the radiation detector 158 has an imaging surface 160 whose area is larger than that of the imaging surface 45 of the radiation detector 26. The number of radiation tubes 159 arranged may increase in order to respond to the capture of the image of a large object.

The detector accommodation portion 155 is inserted below a bed 161 on which the subject H lies supine. The bed 161 is made of a material that transmits the radiation 37. The radiation source accommodation portion 154 is provided above the subject H at a position that faces the detector accommodation portion 155 with the subject H interposed therebetween.

Similarly to the mammography apparatus 10, the imaging apparatus 150 performs pre-imaging using one pre-imaging focus among a plurality of focuses F and performs tomosynthesis imaging using a plurality of radiation tubes 159. The imaging apparatus 150 can perform simple imaging using one radiation tube 159, in addition to the tomosynthesis imaging. In addition, instead of the simple imaging, the imaging apparatus 150 may generate a composite radiographic image. Further, the imaging apparatus 150 may capture both still radiographic images and moving radiographic images. Furthermore, reference numeral 162 indicates a housing for the radiation source 157.

The tomosynthesis imaging apparatus according to the present disclosure may be applied to a general radiography apparatus configured by combining a ceiling-suspended radiation source and an upright imaging table or a decubitus imaging table in which a radiation detector is set, in addition to the imaging apparatus 150 for surgery. Further, the tomosynthesis imaging apparatus according to the present disclosure may be applied to, for example, a cart-type mobile radiography apparatus which is moved to each hospital room and is used to capture the image of the subject H.

In each of the above-described embodiments, each radiation tube 27 has one focus F. However, the technology according to the present disclosure is not limited thereto. At least one of the plurality of radiation tubes 27 may have a plurality of focuses F.

The following first to third configurations are described as the configuration in which one radiation tube has a plurality of focuses. In the first configuration, a plurality of cathodes are provided in one radiation tube and electrons collide with a plurality of different positions of an anode. In the second configuration, a plurality of areas for emitting the electron beams EB are provided in one field-emission-type cold cathode, such as the cathode 35, and electrons collide with a plurality of different positions of an anode. In the third configuration, the trajectory of electrons emitted from one cathode is changed such that electrons collide with a plurality of different positions of an anode. In the first and third configurations, the cathode may be a field-emission-type cold cathode, such as the cathode 35, or a hot cathode in which a filament is heated to emit thermal electrons.

Figure 24:
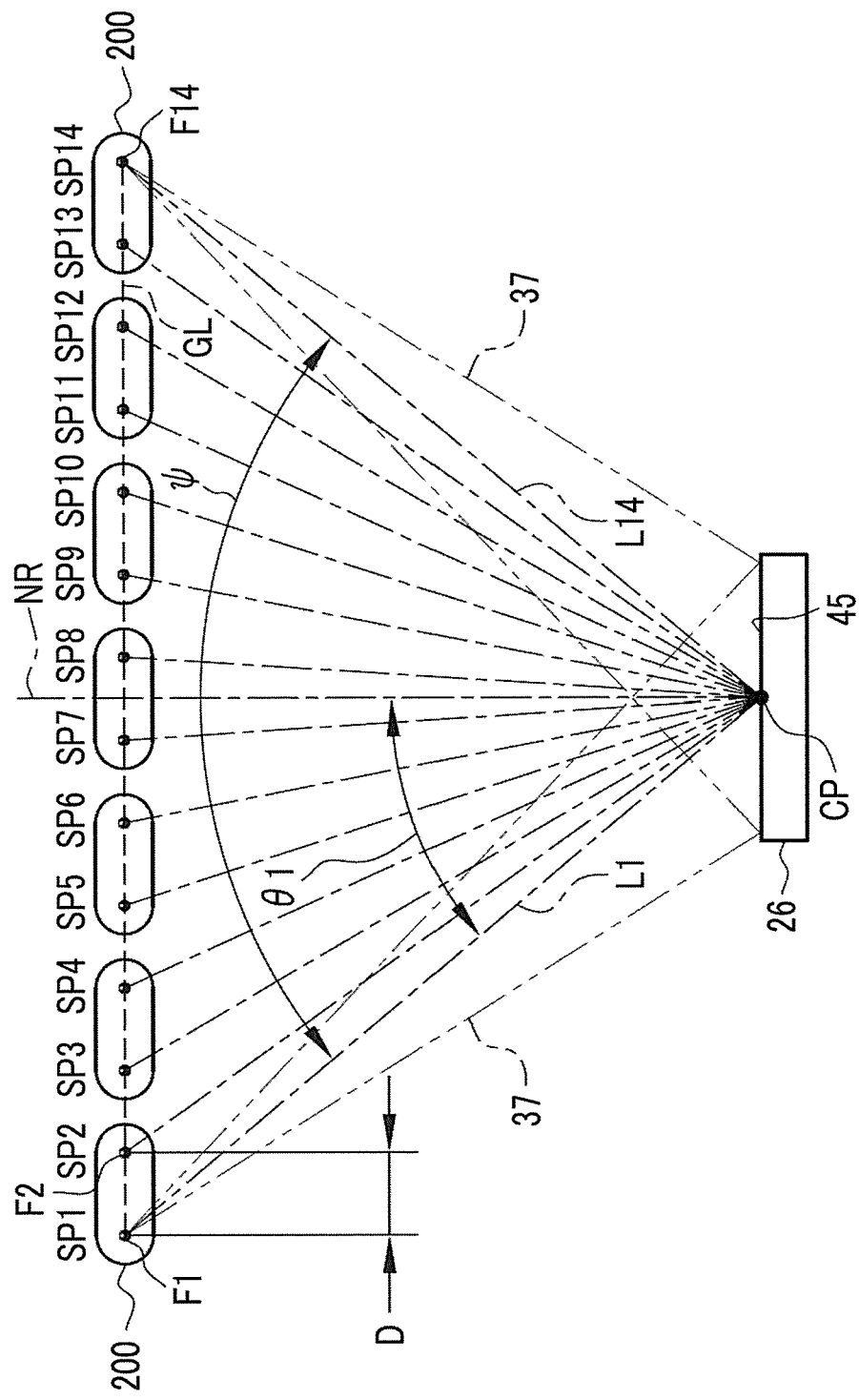
FIG. 24 is a diagram illustrating a configuration of a radiation tube having a plurality of focuses.

FIG. 24 illustrates a case in which radiation tubes 200 each of which has two focuses F are used. That is, a radiation tube 200 having focuses F1 and F2, a radiation tube 200 having focuses F3 and F4, . . . , a radiation tube 200 having focuses F11 and F12, and a radiation tube 200 having focuses F13 and F14 are used. In addition, reference numeral 201 indicates an irradiation field limiter that covers one radiation tube 200.

Figure 25:
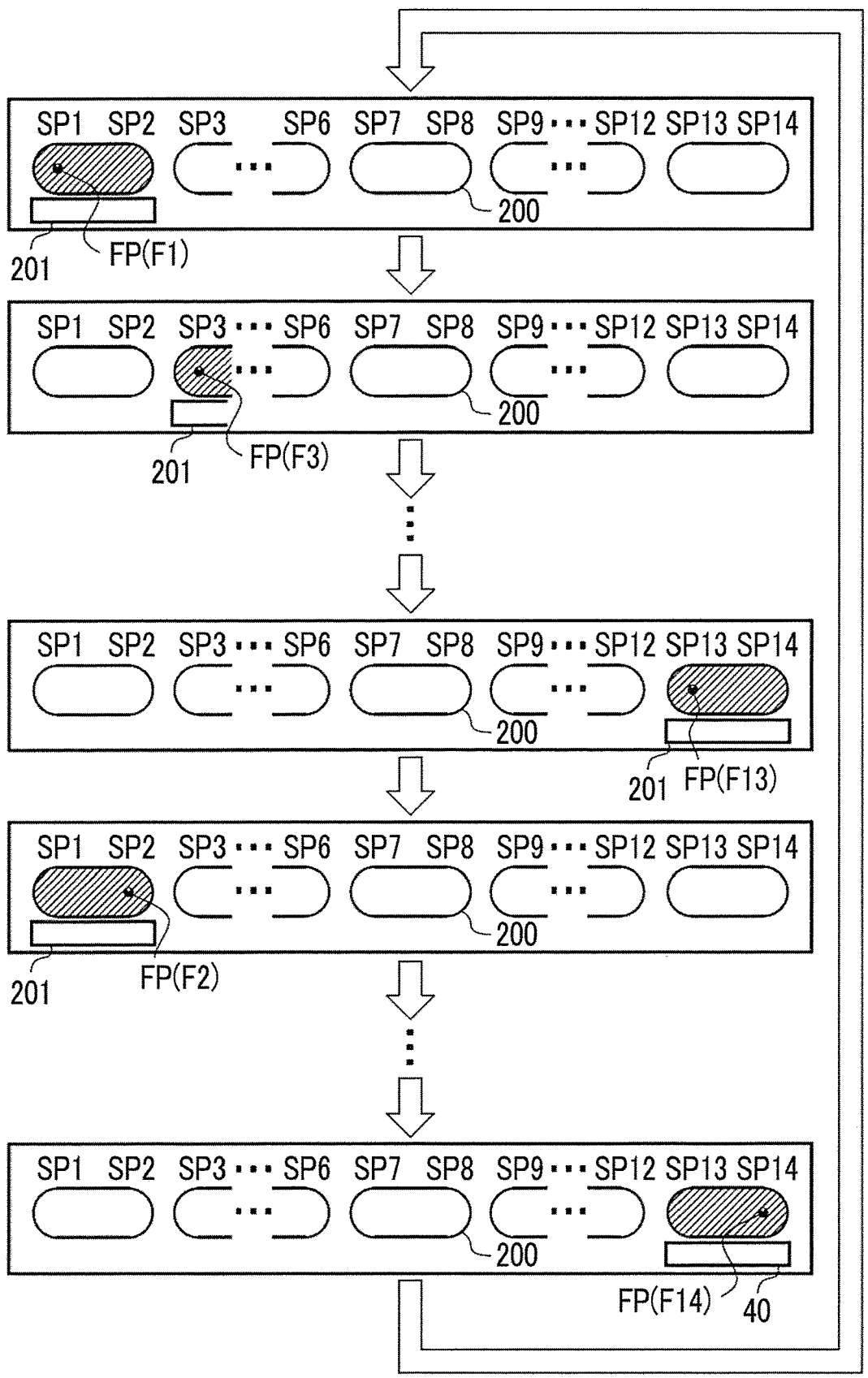
FIG. 25 is a diagram illustrating an example of the change of a pre-imaging focus in the configuration illustrated in FIG. 24.

In the configuration illustrated in FIG. 24, a case is considered in which the selection conditions are, for example, the selection conditions 55 illustrated in FIG. 10 in which the pre-imaging focus FP is changed in each pre-imaging operation and the focus F of a radiation tube disposed adjacent to the radiation tube whose focus has been used as the pre-imaging focus FP in the previous pre-imaging is selected as the pre-imaging focus FP in the next pre-imaging. In this case, for example, the pre-imaging focus FP selected by the pre-imaging control unit 50A is changed as illustrated in FIG. 25. That is, first, the focus F1 of the radiation tube 200 disposed at the positions SP1 and SP2 is used as the pre-imaging focus FP. Then, the focus F3 of the radiation tube 200 disposed at the positions SP3 and SP4 is used as the pre-imaging focus FP. Similarly, the focus F5, the focus F7, . . . , the focus F11, and the focus F13 are sequentially used as the pre-imaging focus FP.

Then, the pre-imaging focus FP returns to the radiation tube 200 disposed at the positions SP1 and SP2 again and not the focus F1 but the focus F2 is used as the pre-imaging focus FP. Then, the focus F4, the focus F6, . . . , the focus F12, and the focus F14 are sequentially used as the pre-imaging focus FP. That is, the pre-imaging focus FP is changed in the order of F1→F3→F5→F7→F9→F11→F13→F2→F4→F6→F8→F10→F12→F14 and returns to the focus F1 again.

In a case in which the second condition of the selection conditions simply indicates that that the focus F which has not been used as the pre-imaging focus FP in the previous pre-imaging is selected as the pre-imaging focus FP in the next pre-imaging, the focuses F1 to F14 may be sequentially selected as the pre-imaging focus FP as in the example illustrated in FIG. 11.

As such, the radiation tube may have a plurality of focuses F. In addition, the radiation source includes a radiation tube having one focus F and a radiation tube having a plurality of focuses F.

In the above-described embodiments, for example, the following various processors can be used as the hardware structure of processing units performing various processes, such as the control unit 50 (the pre-imaging control unit 50A and the tomosynthesis imaging control unit 50B), the irradiation condition setting unit 51, the tomographic image generation unit 52, the acquisition unit 93, and the derivation unit 113. The various processors include a central processing unit (CPU) which is a general-purpose processor executing software to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In the technology according to the present disclosure, the above-mentioned various embodiments and various modification examples may be combined with each other. For example, the selection conditions 55, 65, 75, 85, 105, and 125 described in each of the above-described embodiments may be switched. In addition, the present disclosure is not limited to the above-described embodiments and various configurations can be used without departing from the scope and spirit of the present disclosure.

What is claimed is:

1. A tomosynthesis imaging apparatus comprising:
a radiation detector that detects radiation transmitted through an object and has an imaging surface capturing a projection image of the object;
a radiation source having a plurality of focuses of the radiation disposed at a plurality of positions where the radiation is emitted to the imaging surface at different irradiation angles; and
a control unit that controls an operation of the radiation detector and the radiation source, the control unit being configured to select one pre-imaging focus from the plurality of focuses according to selection conditions which are preset in order to prevent a concentration of load on one of the focuses, and perform tomosynthesis imaging, which captures a plurality of projection images of the object at different irradiation angles using the plurality of focuses, by adjusting at least one of a tube voltage, a tube current or an irradiation time of the tomosynthesis imaging, based on a result of pre-imaging using the selected pre-imaging focus.

2. The tomosynthesis imaging apparatus according to claim 1,
wherein the focuses of the radiation at the plurality of positions are set so as to be arranged in a linear shape or an arc shape at equal intervals.

3. The tomosynthesis imaging apparatus according to claim 2,
wherein the radiation source includes a plurality of radiation tubes, and
at least one of the plurality of radiation tubes has one focus.

4. The tomosynthesis imaging apparatus according to claim 2,
wherein the radiation source includes a plurality of radiation tubes, and
at least one of the plurality of radiation tubes has a plurality of the focuses.

5. The tomosynthesis imaging apparatus according to claim 1,
wherein the selection conditions include a first condition that defines a timing when the pre-imaging focus is changed and a second condition that defines which of the plurality of focuses is selected as the pre-imaging focus.

6. The tomosynthesis imaging apparatus according to claim 5,
wherein the first condition indicates that the pre-imaging focus is changed in each pre-imaging operation.

7. The tomosynthesis imaging apparatus according to claim 5, wherein the first condition indicates that the pre-imaging focus is changed in a case in which the pre-imaging is continuously performed a set number of times using the same pre-imaging focus.

8. The tomosynthesis imaging apparatus according to claim 5,
wherein the first condition indicates that the pre-imaging focus is changed in a case in which an actual value of a cumulative dose of the radiation in the pre-imaging became greater than a set value after the pre-imaging focus is changed in previous pre-imaging.

9. The tomosynthesis imaging apparatus according to claim 5,
wherein the second condition indicates that a focus which has not been used as the pre-imaging focus in the previous pre-imaging is selected as the pre-imaging focus in next pre-imaging.

10. The tomosynthesis imaging apparatus according to claim 5,
wherein the radiation source includes a plurality of radiation tubes each of which has at least one focus, and
the second condition indicates that a focus of a radiation tube adjacent to the radiation tube whose focus has been used as the pre-imaging focus in the previous pre-imaging is selected as the pre-imaging focus in the next pre-imaging.

11. The tomosynthesis imaging apparatus according to claim 5,
wherein the radiation source includes a plurality of radiation tubes each of which has at least one focus,
the tomosynthesis imaging apparatus further comprises an acquisition unit that acquires a temperature of each of the plurality of radiation tubes, and
the second condition indicates that a focus of a radiation tube with a lowest temperature is selected as the pre-imaging focus in the next pre-imaging.

12. The tomosynthesis imaging apparatus according to claim 5, further comprising:
a derivation unit that derives a degree of deterioration of a performance of each of the plurality of focuses on the basis of a usage history of each of the plurality of focuses,
wherein the second condition indicates that a focus with a smallest degree of deterioration is selected as the pre-imaging focus in the next pre-imaging.

13. The tomosynthesis imaging apparatus according to claim 5,
wherein the tomosynthesis imaging apparatus is a mammography apparatus that uses a breast as the object.

14. The tomosynthesis imaging apparatus according to claim 13,
wherein the first condition indicates that the pre-imaging focus is changed according to imaging methods including craniocaudal imaging which captures an image of the breast compressed in a vertical direction, right mediolateral oblique imaging which captures an image of a right breast compressed obliquely, and left mediolateral oblique imaging which captures an image of a left breast compressed obliquely, and
the second condition indicates that a focus closest to a position of a center of a maximum scanning angle of the tomosynthesis imaging which is defined by positions at both ends among the plurality of positions is selected as the pre-imaging focus in the craniocaudal imaging, a focus which is disposed at a position close to a right axilla of the positions at both ends is selected as the pre-imaging focus in the right mediolateral oblique imaging, and a focus which is disposed at a position close to a left axilla of the positions at both ends is selected as the pre-imaging focus in the left mediolateral oblique imaging.

15. The tomosynthesis imaging apparatus according to claim 1, further comprising:
an irradiation field limiter which sets an irradiation field of the radiation, whose number is less than the number of the plurality of focuses, and whose position is configured to be moved,
wherein, before the next pre-imaging starts, the irradiation field limiter is moved to a position of the pre-imaging focus in the next pre-imaging to set the irradiation field.

16. The tomosynthesis imaging apparatus according to claim 1, further comprising:
irradiation field limiters that set an irradiation field of the radiation, are provided for each of the plurality of focuses, and are configured to be individually operated,
wherein, before the next pre-imaging starts, the irradiation field limiter corresponding to the pre-imaging focus in the next pre-imaging is operated to set the irradiation field.

17. The tomosynthesis imaging apparatus according to claim 1,
wherein the radiation source includes a cathode that emits electrons and an anode with which the electrons collide and which emits the radiation.

18. The tomosynthesis imaging apparatus according to claim 17,
wherein the anode is a fixed anode.

19. The tomosynthesis imaging apparatus according to claim 17,
wherein the cathode is a field emission type including an electron emission source that emits an electron beam using a field emission phenomenon.

20. The tomosynthesis imaging apparatus according to claim 1,
wherein the control unit is configured to perform the tomosynthesis imaging, which captures the plurality of projection images of the object at the different irradiation angles using the plurality of focuses, by adjusting at least one of the tube voltage, the tube current or the irradiation time of the tomosynthesis imaging, based on a density of an image obtained by the pre-imaging.

21. A method for operating a tomosynthesis imaging apparatus comprising a radiation detector that detects radiation transmitted through an object and has an imaging surface capturing a projection image of the object and a radiation source having a plurality of focuses of the radiation disposed at a plurality of positions where the radiation is emitted to the imaging surface at different irradiation angles, the method comprising:
selecting one pre-imaging focus from the plurality of focuses according to selection conditions which are preset in order to prevent a concentration of load on one of the focuses and performing pre-imaging using the selected pre-imaging focus; and
performing tomosynthesis imaging, which captures a plurality of projection images of the object at different irradiation angles using the plurality of focuses, by adjusting at least one of a tube voltage, a tube current or an irradiation time of the tomosynthesis imaging, based on a result of the pre-imaging.

22. A non-transitory computer-readable storage medium storing a program for operating a tomosynthesis imaging apparatus comprising a radiation detector that detects radiation transmitted through an object and has an imaging surface capturing a projection image of the object and a radiation source having a plurality of focuses of the radiation disposed at a plurality of positions where the radiation is emitted to the imaging surface at different irradiation angles, the program causing a computer to execute a process comprising:

selecting one pre-imaging focus from the plurality of focuses according to selection conditions which are preset in order to prevent a concentration of load on one of the focuses and performing pre-imaging using the selected pre-imaging focus; and performing tomosynthesis imaging, which captures a plurality of projection images of the object at different irradiation angles using the plurality of focuses, by adjusting at least one of a tube voltage, a tube current or an irradiation time of the tomosynthesis imaging, based on a result of the pre-imaging.

* * * * *